(12) United States Patent
Hoffmann et al.

(10) Patent No.: US 10,682,290 B2
(45) Date of Patent: Jun. 16, 2020

(54) KIT OF PARTS FOR CONDUCTING A DENTAL IMPRESSION AND RETRACTION PROCESS

(71) Applicant: 3M INNOVATIVE PROPERTIES COMPANY, St. Paul, MN (US)

(72) Inventors: Henning Hoffmann, Windach (DE);
Peter U. Osswald, Tuerkheim (DE);
Joachim W. Zech, Kaufering (DE);
Andreas R. Maurer, Langenneufnach (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 177 days.

(21) Appl. No.: 15/574,871

(22) PCT Filed: May 23, 2016

(86) PCT No.: PCT/US2016/033699
§ 371 (c)(1),
(2) Date: Nov. 17, 2017

(87) PCT Pub. No.: WO2016/196048
PCT Pub. Date: Dec. 8, 2016

(65) Prior Publication Data
US 2018/0125764 A1 May 10, 2018

(30) Foreign Application Priority Data
May 29, 2015 (EP) ..................................... 15169805

(51) Int. Cl.
*A61K 6/90* (2020.01)
*A61K 6/15* (2020.01)
(Continued)

(52) U.S. Cl.
CPC .................. *A61K 6/90* (2020.01); *A61K 6/15* (2020.01); *A61K 6/19* (2020.01); *C08L 51/085* (2013.01); *C08L 83/04* (2013.01)

(58) Field of Classification Search
None
See application file for complete search history.

(56) References Cited

U.S. PATENT DOCUMENTS

| | | |
|---|---|---|
| 3,242,218 A | 3/1966 | Miller |
| 3,715,334 A | 2/1973 | Karstedt |

(Continued)

FOREIGN PATENT DOCUMENTS

| | | |
|---|---|---|
| CA | 2517094 | 8/2004 |
| EP | 0231420 | 8/1987 |

(Continued)

OTHER PUBLICATIONS

Shih, "Synthesis and characterization of polycarbonate/polydimethylsiloxane multiblock copolymer prepared from dimethylsiloxane and various aromatic dihydroxyl monomer", Journal of Applied Polymer Science, Jan. 2000, vol. 75, No. 4, pp. 545-552.

(Continued)

*Primary Examiner* — Peter A Salamon
(74) *Attorney, Agent, or Firm* — 3M Innovative Properties Company

(57) ABSTRACT

The present invention relates to a kit of parts comprising Paste (A), Paste (B) and Paste (C), the pastes being characterized as follows: Paste (A) comprising at least one polyorganosiloxane with at least two olefinically unsaturated groups, and at least one organohydrogenpolysiloxane, at least one alkylsiloxane having at least one carbinol, silanol, alkoxy, carboxyl or amino group, optionally filler(s) and optionally additive(s); Paste (B) comprising at least one (Continued)

polyorganosiloxane optionally with olefinically unsaturated groups, at least one addition cure catalyst, optionally at least one alkylsiloxane having at least one carbinol, silanol, alkoxy, carboxyl or amino group, optionally filler(s) and optionally additive(s) Paste (C) comprising a softener, a condensation cure catalyst, optionally filler(s), and optionally additive(s) optionally at least one polyorganosiloxane optionally with olefinically unsaturated groups. The invention is also directed to a system for storing and delivering Paste (A), Paste (B) and Paste (C), the system comprising three compartments for storing the respective pastes, means for delivering the respective pastes to an outlet orifice and an interface for receiving a mixing tip. The kit of parts or the system is in particular useful for conducting a dental retraction and dental impression process.

22 Claims, 1 Drawing Sheet

(51) Int. Cl.
*A61K 6/19* (2020.01)
*C08L 51/08* (2006.01)
*C08L 83/04* (2006.01)

(56) References Cited

U.S. PATENT DOCUMENTS

| | | | | |
|---|---|---|---|---|
| 3,760,503 A * | 9/1973 | Baskas | ............... | A61B 17/8825 433/90 |
| 3,775,352 A | 11/1973 | Leonard | | |
| 3,814,730 A | 6/1974 | Karstedt | | |
| 3,933,880 A | 1/1976 | Bergstrom | | |
| 4,035,453 A * | 7/1977 | Hittmair | ............... | A61K 6/10 264/16 |
| 4,159,570 A * | 7/1979 | Baskas | ............... | A61C 9/0026 206/222 |
| 4,273,902 A | 6/1981 | Tomioka | | |
| 4,538,920 A * | 9/1985 | Drake | ............... | B01F 5/0615 222/137 |
| 4,657,959 A | 4/1987 | Bryan | | |
| 4,778,832 A * | 10/1988 | Futami | ............... | A61K 6/10 106/35 |
| 4,782,101 A | 11/1988 | Waller | | |
| 5,159,096 A | 10/1992 | Austin | | |
| 5,249,862 A | 10/1993 | Herold | | |
| 5,286,105 A | 2/1994 | Herold | | |
| 5,464,131 A | 11/1995 | Keller | | |
| 5,684,060 A | 11/1997 | Konings | | |
| 5,750,589 A | 5/1998 | Zech | | |
| 5,849,812 A * | 12/1998 | Zech | ............... | A61K 6/10 523/109 |
| 5,907,002 A * | 5/1999 | Kamohara | ............... | A61K 6/10 106/35 |
| 6,040,354 A * | 3/2000 | Hubner | ............... | A61K 6/10 264/16 |
| 6,312,254 B1 | 11/2001 | Friedman | | |
| 6,677,393 B1 | 1/2004 | Zech | | |
| 7,097,452 B2 | 8/2006 | Friedman | | |
| 8,047,841 B2 | 11/2011 | Jefferies | | |
| 9,694,383 B2 | 7/2017 | Jurcevic | | |
| 2002/0147275 A1 * | 10/2002 | Bublewitz | ............... | A61K 6/10 525/100 |
| 2002/0156186 A1 * | 10/2002 | Bublewitz | ............... | A61K 6/10 525/100 |
| 2004/0124396 A1 | 7/2004 | Flynn | | |
| 2005/0027032 A1 | 2/2005 | Hare | | |
| 2005/0186531 A1 | 8/2005 | Friedman | | |
| 2005/0186532 A1 | 8/2005 | Friedman | | |
| 2005/0239958 A1 * | 10/2005 | Bublewitz | ............... | A61K 6/10 524/862 |
| 2006/0293469 A1 * | 12/2006 | Zech | ............... | A61K 6/10 525/477 |
| 2007/0060717 A1 * | 3/2007 | Zech | ............... | A61K 6/10 525/478 |
| 2008/0200584 A1 | 8/2008 | Bottcher | | |
| 2008/0249205 A1 * | 10/2008 | Kamohara | ............... | A61K 6/10 523/109 |
| 2010/0035213 A1 | 2/2010 | Lubbers | | |
| 2010/0184881 A1 * | 7/2010 | Zech | ............... | A61K 6/10 523/109 |
| 2011/0098435 A1 * | 4/2011 | Hofmann | ............... | C07F 15/0046 528/25 |
| 2012/0083549 A1 * | 4/2012 | Kamohara | ............... | A61K 6/10 523/109 |
| 2012/0315601 A1 * | 12/2012 | Shchori | ............... | A61K 6/087 433/199.1 |
| 2013/0230676 A1 * | 9/2013 | Blizzard | ............... | C08G 77/58 428/36.9 |
| 2014/0050043 A1 | 2/2014 | Durali | | |
| 2014/0170596 A1 | 6/2014 | Angeletakis | | |
| 2015/0230900 A1 | 8/2015 | Gente | | |
| 2018/0125764 A1 * | 5/2018 | Hoffmann | ............... | A61K 6/0014 |

FOREIGN PATENT DOCUMENTS

| | | |
|---|---|---|
| EP | 0480238 | 4/1992 |
| EP | 0639622 | 2/1995 |
| EP | 0730913 | 9/1996 |
| EP | 1502572 | 2/2005 |
| EP | 1596752 | 11/2005 |
| EP | 1776080 | 4/2007 |
| EP | 2030604 | 3/2009 |
| EP | 2133038 | 12/2009 |
| EP | 2231102 | 9/2010 |
| EP | 2529690 | 12/2012 |
| EP | 2698124 | 2/2014 |
| WO | WO 1996-04334 | 2/1996 |
| WO | WO 1997-03110 | 1/1997 |
| WO | WO 2002-058641 | 8/2002 |
| WO | WO 2004-071326 | 8/2004 |
| WO | WO 2004-082508 | 9/2004 |
| WO | WO 2005-013925 | 2/2005 |
| WO | WO 2007-001869 | 1/2007 |
| WO | WO 2008-059468 | 5/2008 |
| WO | WO 2013-190457 | 12/2013 |
| WO | WO 2014-008894 | 1/2014 |
| WO | WO 2014-044711 | 3/2014 |
| WO | WO 2016-196027 | 12/2016 |
| WO | WO 2016-196028 | 12/2016 |
| WO | WO 2017-007676 | 1/2017 |

OTHER PUBLICATIONS

Kugel, "Investigation of a New Approach to Measuring Contact Angles for Hydrophilic Impression Materials", Journal of Prosthodontics, 2007, vol. 16, No. 2, pp. 84-92.
International Search Report for PCT International Application No. PCT/US2016/033699, dated Jun. 30, 2016, 4 pages.

* cited by examiner

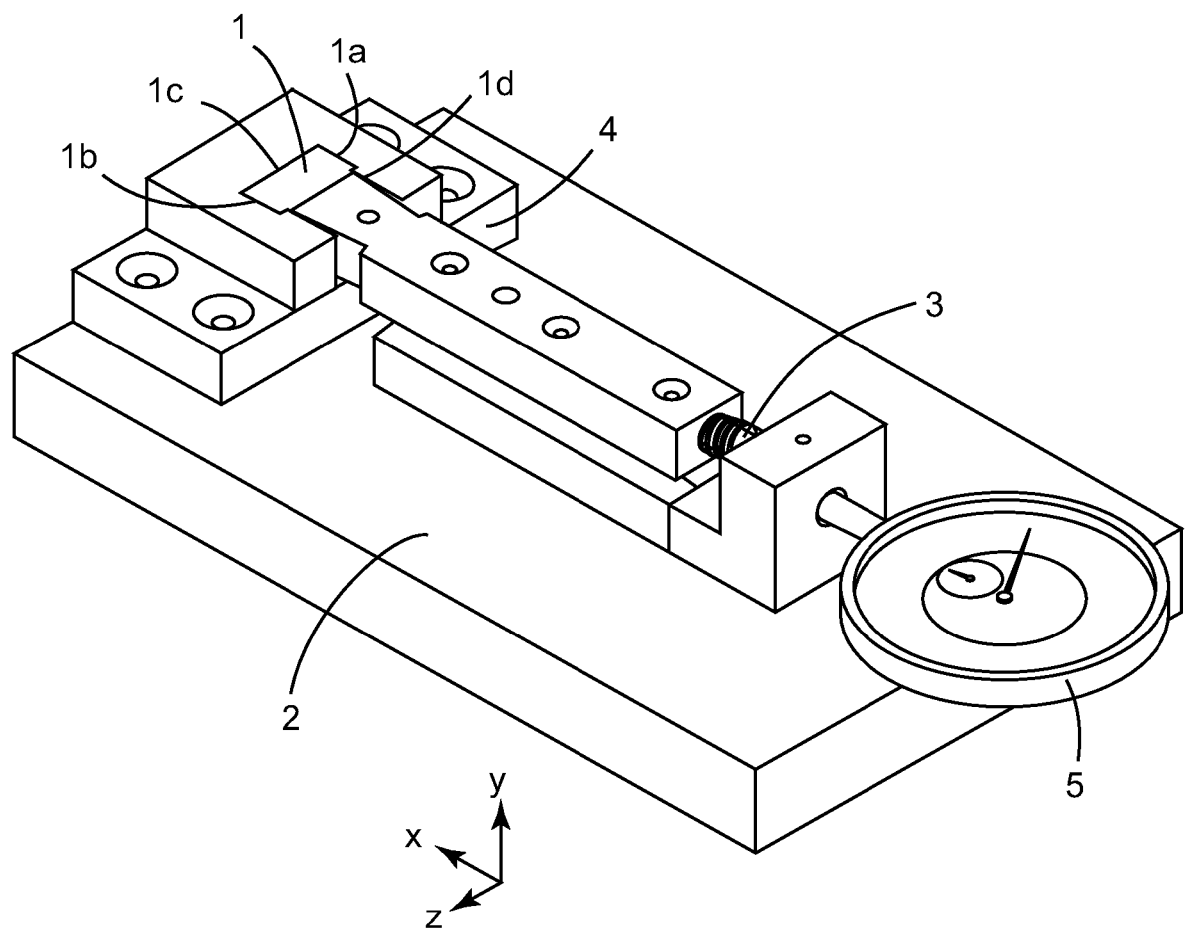

KIT OF PARTS FOR CONDUCTING A
DENTAL IMPRESSION AND RETRACTION
PROCESS

FIELD OF THE INVENTION

The invention relates to kit of parts comprising three pastes to be mixed for conducting a dental impression and retraction process. The invention also relates to a process for applying different mixtures of these three pastes onto the surface of dental tissue.

BACKGROUND ART

For producing an accurate dental restoration it is important to have the margin of the preparation of the teeth clearly visible in a dental impression. Therefore, it is often recommended to widen the sulcus in a retraction process. This is typically done by using a retraction cord or a retraction paste before the dental impression step is conducted.

This retraction step is an additional, often time consuming and sometimes difficult step to perform for the dental practitioner.

A good retraction material has the ability to keep the sulcus of a tooth open and withstand the forces of the surrounding soft dental tissue. In this respect, often pastes having a high viscosity are suggested.

However, a material having a high viscosity is not suitable as dental impression material, as this material is typically not able to reproduce the fine contours (precision) on the teeth surface, a property needed for producing an accurate dental restoration.

Technical solutions known today typically require separate pastes or materials for conducting either the dental retraction or dental impressioning process. Known are compositions which increase the viscosity upon mixture by combining two setting mechanisms.

US 2005/239958 A1 (Bublewitz et al.) describes a two-step curable mixer-suitable material for making dental impressions. The system contains at least one compound having at least two alkenyl groups, at least one organohydrogenpolysiloxane, at least one hydrosilylation catalyst, wherein at least one polymeric compound having at least one alkynyl group, at least one compound having at least one Si—OR structural unit and at least one condensation catalyst is contained.

WO 2005/013925 A1 (3M) relates to an automixable putty impression material. The composition comprises at least one polydiorganoxiloxane having at least two aliphatically unsaturated groups, at least one organohydrogenpolysiloxane, at least one alkylsiloxane having at least one carbinol, carboxy or amino group, at least one condensation cure compound and at least one addition cure precious metal catalyst.

US 2008/0200584 A1 (Bottcher et al.) describes a silicone impression material with two-stage curing mechanism. The impression material comprises at least one compound (a) with at least two alkenyl groups, at least one compound (b) with at least one chelating group, at least one organohydropolysiloxane (c), at least one hydrosilylation catalyst (d) and at least one compound with a chelatable metal component (e), the chelating group exhibiting no reactive groups which can react with component (c) and/or component (d).

EP 1 776 080 B1 (Dentsply) is directed to a method of taking a dental impression of a dentition including sub-gingival parts, comprising the steps of (i) conditioning the dentition including sub-gingival parts by application thereto of a wetting agent comprising a surfactant and a carrier; (ii) contacting the dentition with a dental impression material selected from hydrophilic and hydrophobic dental impression materials, whereby the impression material is allowed to flow into sub-gingival parts, further comprising the step of preparing the dentition with a gingival retraction cord, wherein said gingival retraction cord has been contacted with a wetting agent further comprising a hemostatic agent. Known are also references dealing with dental retraction pastes.

US 2014/0170596 A1 (Angeletakis) describes a two part retraction system than be inserted into the sulcus to form a semi-rigid porous elastomer releasing a hemostatic agent suitable for sulcus retraction such that a dental impression may be completed by a dental practitioner.

US 2010/0035213 A1 (Lubbers et al.) describes a dental kit and method for retracting sulcus. The method comprises the steps of (i) molding a dental impression of a portion of the patients mouth with a curable composition, (ii) removing the cured mold, (iii) applying an expanding silicone material with expands during curing to the adjacent area between the tooth and gingiva and (iv) reapplying the mold to the mouth of the patient to form a barrier to the expansion of the silicone material to limit the expansion of the silicon only in the direction toward the sulcus. None of the solutions described in the prior art is satisfactory.

DESCRIPTION OF THE INVENTION

It would be desirable to simplify the dental impressioning and dental retraction process.

In particular, a material is desired which can be used as not only as dental retraction material but also as dental impression material.

This invention addresses this issue and reduces the efforts of the dentist to provide an accurate dental impression of the dental situation of a patient.

This can be accomplished by providing a three composition system which includes two separate setting mechanisms, which gives the dentist the freedom to control the viscosity of the mixed paste, by adding the third composition to the mixture of the other two compositions thereby increasing the viscosity.

In one embodiment the present invention features a kit of parts comprising Paste (A), Paste (B) and Paste (C), the pastes being characterized as follows:

Paste (A) comprising:
at least one polyorganosiloxane with at least two olefinically unsaturated groups as component (a),
at least one organohydrogenpolysiloxane as component (b),
at least one alkylsiloxane having at least one carbinol, silanol, alkoxy, carboxyl or amino group as component (c),
Paste (A) comprising in addition
optionally filler(s) as component (h) and
optionally additive(s) as component (i);
Paste (B) comprising:
at least one polyorganosiloxane (optionally with olefinically unsaturated groups) as component (d),
at least one addition cure catalyst as component (e),
optionally at least one alkylsiloxane having at least one carbinol, silanol, alkoxy, carboxyl or amino group,
optionally filler(s) as component (h) and
optionally additive(s) as component (i);

Paste (C) comprising:
- a softener as component (f)
- a condensation cure catalyst as component (g),
- optionally filler(s) as component (h), and
- optionally additive(s) as component (i).

The at least one polyorganosiloxane with at least two olefinically unsaturated groups as component (a), the at least one organohydrogenpolysiloxane as component (b) and the at least one polyorganosiloxane (optionally with olefinically unsaturated groups) as component (d) form a curable matrix (I) which starts to harden, if combined with addition cure catalyst component (e).

The at least one alkylsiloxane having at least one carbinol, silanol, carboxyl or amino group as component (c) forms a curable matrix (II) which starts to harden, if combined with condensation cure catalyst component (g).

In another embodiment, the invention relates to a process for taking a dental impression of a dental situation including sub-gingival parts of the sulcus, the process comprising the steps of
- a) providing the kit of parts as described in any of the proceeding claims,
- b) mixing Paste (A), Paste (B) and Paste (C) to obtain Composition (ABC),
- c) applying Composition (ABC) into the sulcus of the dental situation,
- d) mixing Paste (A) and Paste (B) to obtain Composition (AB),
- e) applying Composition (AB) in contact with Composition (ABC),
- f) optionally applying a further Composition (D) being different from Composition (AB) and Composition (ABC) in contact with Composition (AB),
- g) removing Composition (ABC) and Composition (AB) and Composition (D), if present, from the dental situation.

The invention is also related to the use of the kit of parts as described in the present text for conducting a dental retraction and dental impression process.

The invention is also directed to a system for storing and delivering Paste A, Paste B and Paste C as described in the present text, the system comprising three compartments for storing the respective pastes, means for delivering the respective pastes to an outlet orifice and an interface for receiving a mixing tip.

Definitions

Unless defined differently, for this description the following terms shall have the given meaning:

A "dental composition" or a "composition for dental use" or a "composition to be used in the dental field" is any composition which can be used in the dental field. In this respect the composition should not be detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices. Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health. Dental compositions are typically provided to the practitioner in comparable small volumes, that is volumes in the range from about 0.1 to about 500 ml or from about 0.5 to about 100 ml or from about 1 to about 50 ml. Thus, the storage volume of useful packaging devices is within these ranges.

A "dental impression material" is a material used for making impressions of the tooth structure including the gingiva. A dental impression material is usually applied on a dental impression tray. A dental impression material can be based on different chemical substances and crosslink by various chemical reactions (including addition curing and condensation curing materials). Typical examples include silicone based impression materials (e.g. VPS materials) and polyether based impression materials and mixtures of those.

A "putty like dental impression material" is a kneadable dental impression material having a consistency of 35 mm or below according to ISO 4823.

A "dental retraction material" is a material intended to be placed in the gingival sulcus, that is, the natural space between the hard dental tissue (i.e. tooth structure) and the gum tissue that surrounds the hard dental tissue. Once placed in the gingival sulcus, the dental retraction material will exert pressure on the surrounding tissue resulting in a widening of the gingival sulcus to enable the practitioner to get a more precise impression of the dental situation below the gum line during a dental impression process. Like a dental impression material, a dental retraction material is removed from the mouth of the patient after use.

"Dental situation" means a part or all of a person's dentition and surrounding structures in the oral cavity, including subgingival portions.

"Dental tissue" means the hard and soft dental tissue. Hard dental tissue comprises the tissue of dental tooth (including dentin and enamel). Soft dental tissue comprises the tissue surrounding the hard dental tissue, i.e. the gum.

The term "compound" or "component" is a chemical substance which has a particular molecular identity or is made of a mixture of such substances, e.g., polymeric substances.

A "liquid" is any solvent or liquid which is able to at least partially disperse, dissolve or suspend the components being present in the inventive composition at ambient conditions (e.g. 23° C.).

By "paste" is meant a soft, viscous mass of solids (i.e. particles) dispersed in a liquid.

A "particle" or "particulate filler" means a substance being a solid having a shape which can be geometrically determined. The shape can be regular or irregular. Particles can typically be analysed with respect to e.g. grain size and grain size distribution. A particulate filler is composed of free-flowing particles.

"Room temperature hardening or curing" implies that the curing reaction can proceed at temperatures at or near 25° C. For example, the oral cavity of the mouth has an average temperature of approximately 32° C. and is therefore near room temperature. Certain "high" temperature cured materials are designed to cure only at relatively high temperatures (e.g., >50° C. or >100° C.) and are stable (i.e., the curing reaction is inhibited) at room temperature.

The term "silicone," as used herein, refers to a polymer having, for the most part, alternating silicon and oxygen atoms (i.e., a polysiloxane chemical structure) and having sufficient pendant functional groups to undergo a setting reaction in the presence of a crosslinker compound and a catalyst compound. A "silicone elastomer" is an elastomeric polymer comprising silicone units, i.e. comprising the elements Si, O, C and H, in particular dimethylsiloxane (—O—$Si(CH_3)_2$—) units.

"Elastomeric" means rubber-elastic or rubber-like. Elastomeric materials can be characterized e.g. by a certain tensile or tear strength and/or elongation at break. Other means for characterizing elastomeric materials include the measurement e.g. of the Young's modulus. Elastomeric materials typically have an E-modulus in the range from 0.8 to 10 MPa or from 1 to 8 MPa or from 1.5 to 6 MPa (determined e.g. according to DIN 53504, thickness of sample: 2 mm).

"Poly" means that the respective substance contains at least 10 repeating units of a certain monomer moiety.

The term "hydrosilation" means the addition of a compound comprising SiH-groups to a compound containing an aliphatic multiple bond (e.g., an olefinically or acetylenic unsaturation), preferably a vinyl group, —CH=CH$_2$.

The terms "vulcanizing, hardening, crosslinking, setting, curing" are used interchangeable and refer to silicones that have as a common attribute the development of a cross-linked elastomer from relatively low molecular weight linear or branched polymers by means of a chemical reaction that simultaneously forms these crosslinks and effectively extends chain length at room temperature.

"Hydrophilating agents" are agents that are able to either lower the surface tension of water, if used alone (like surfactants), or contribute to a lower surface tension, if used in combination with a surfactant (sometimes referred to as wetting-enabler). If desired, the effect of lowering the surface tension of water can be measured by determining the water-contact angle as described in more detail below.

The term "automixer-suitable material" relates to a multi-component material which can be dispensed, for example, from a two-component disposable cartridge through a static mixer, e.g., of SulzerMixpac Company (cf. U.S. Pat. No. 5,464,131, EP 0 730 913 A1) or from film bags in dual-chamber reusable cartridges through a dynamic mixer, e.g., in the "Pentamix™", "Pentamix™ 2" and "Pentamix™ 3" devices of 3M ESPE Company (cf. U.S. Pat. Nos. 5,286,105 and 5,249,862).

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory ambient conditions are adjusted to 20 to 25° C. and 1000 to 1025 mbar.

A composition is "essentially or substantially free of" a certain component, if the composition does not contain said component as an essential feature. Thus, said component is not wilfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about". The term "comprise" shall include also the terms "consist essentially of" and "consists of".

BRIEF DESCRIPTION OF FIGURES

FIG. 1 shows a device which can be used for determining the rheological properties of the curable composition (e.g. flowing properties of the composition under a predefined load if placed in a predefined mould).

DETAILED DESCRIPTION OF THE INVENTION

The composition obtained when mixing the pastes contained in the kit of parts described in the present text include two different setting mechanisms.

Those different setting mechanisms are initiated by using two different kind of starter or catalyst components. The different kind of starter or catalyst components are present in two of the three paste compositions of the kit of parts.

By adding the second starter or catalyst component to the other paste compositions, an additional setting reaction is initiated. This additional setting reaction has an impact on the development of viscosity or consistency of the curable composition.

Thus, the kit of parts described in the present text enables the practitioner to adjust the viscosity of the resulting mixture on demand.

The kit of parts and process described in the present text makes it possible to use one material composition on the one hand in a thick viscosity stage for conducting a dental retraction step and on the other hand using a second material composition in a thin viscosity stage for conducting a dental impression step.

By mixing only Composition (A) and Composition (B) to obtain Composition (AB) a conventional VPS dental impression material can be obtained, which has a sufficiently low viscosity allowing the material to be used as a so-called wash material in a process for taking a dental impression.

On demand, the third Composition (C) is added to the other compositions to obtain Composition (ABC). Composition (ABC) now contains two different curing catalyst or starters, a condensation cure catalyst and an addition cure catalyst.

Due to the presence of two different catalysts or starters, the viscosity of Composition (ABC) is increased in a short period of time. A high viscous paste is obtained which is useful for conducting a retraction step. The obtained paste has a viscosity or consistency sufficiently high to enable the dentist to apply this paste into the sulcus of tooth and to keep the sulcus open.

The composition obtained when mixing Composition (A) and Composition (B) of the kit of parts as described in the text is in particular useful as dental impression material and to obtain a dental impression of the dental situation in the mouth of a patient.

The composition obtained when mixing Composition (A), Composition (B) and Composition (C) of the kit of parts as described in the text is useful as dental retraction material. Such a material cannot only be inserted into the sulcus, but also has a sufficiently high viscosity or consistency to keep the sulcus open.

In contrast to the invention described in the present text, the compositions suggested in prior art references like US 2005/0239958 A1 (Bublewitz et al.) and WO 2005/013925 A1 (3M) deal with machine mixable high viscous impression materials which are not adjustable in viscosity due to their fixed two component mixing ratio. In these inventions two low viscous pastes are mixed by a dynamic mixing machine and during the mixing process one setting mechanism increases the viscosity of the paste to a kneadable consistency.

The kit of parts described in the present text comprises three paste compositions: Paste (A), Paste (B) and Paste (C).

Paste (A) comprises components of two organic hardenable matrices, matrix (I) and matrix (II). Further components of the hardenable matrices are present either in Paste (B) or Paste (B) or in Paste (B) and Paste (C).

The curable components of matrix (I) harden according to a different curing mechanism than the curable components of matrix (II). The curable components of matrix (I) are curable by an addition reaction, whereas the curable components of matrix (II) are curable by a condensation reaction.

To effect curing of the composition obtained when combining Paste (A) and Paste (B), two different catalysts or initiators are needed.

The catalyst needed for curing component (a) and component (b) is present in Paste (B).

The catalyst needed for curing component (c) is present in Paste (C).

During the use of the pastes contained in the kit of parts, different mixtures of those compositions are provided.

In a first step Paste (A), Paste (B) and Paste (C) are mixed to obtain Composition (ABC).

In a second step Paste (A) and Paste (B) are mixed to obtain Composition (AB).

The individual compositions can be characterized as follows:

In certain embodiments Paste (A) fulfils at least one or more, sometimes all of the following parameters:
- having a consistency according to ISO 4823 in the range from 25 to 50 mm;
- having a water contact angle, measured 10 s after placing a drop of water onto the surface of the paste of <90°.

Paste (A) comprises
- at least one polyorganosiloxane with at least two olefinically unsaturated groups as component (a),
- at least one organohydrogenpolysiloxane as component (b),
- at least one alkylsiloxane having at least one carbinol, silanol, carboxyl or amino group as component (c),
- optionally filler(s) as component (h) and
- optionally additive(s) as component (i).

The nature and structure of component (a) is not particularly limited unless the desired result cannot be achieved. The hardening of component (a) is effected by a polyaddition reaction.

This curing mechanism is typically based upon the polyaddition of silanes with aliphatically unsaturated double bonds (e.g. vinyl groups) in the presence of a catalyst, such as Pt containing compound. The respective compositions are often referred to as VPS materials and the curing mechanism as hydrosilation.

The organopolysiloxane is a molecule in which at least two organic groups are groups with an ethylenically unsaturated double bond. Generally, the groups with an ethylenically unsaturated double bond can be located on any monomeric unit of the organopolysiloxane. It can, however, be preferred, that the groups with an ethylenically unsaturated double bond are located on or at least near the terminal monomeric units of the polymer chain of the organopolysiloxane. In another embodiment, at least two of the groups with an ethylenically unsaturated double bond are located on the terminal monomeric units of the polymer chain.

The term "monomeric units" as used throughout the present text relates to repeating structural elements in the polymer that form the polymer backbone, unless expressly stated otherwise.

Preferred organopolysiloxanes of this general structure are represented by the following formula (I)

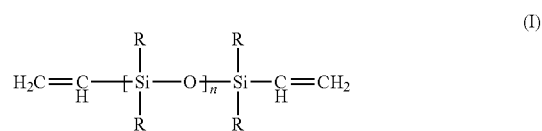

in which the radicals R, independently from each other, represent a non-substituted or substituted, monovalent hydrocarbon group with 1 to 6 C atoms, which is preferably free from aliphatic multiple bonds and where n generally can be chosen such that the viscosity of the organopolysiloxanes lies between 4 and 1,000,000 mPas or between 6 and 500,000 or between 10 and 100,000 mPas. The parameter n can, e.g., be in the range of 10 to 10,000.

Generally, the radicals R in the above formula can represent any non-substituted or substituted, monovalent hydrocarbon group with 1 to about 6 C atoms. Non-substituted or substituted, monovalent hydrocarbon groups with 1 to about 6 C atoms can be linear or, if the number of carbon atoms exceeds 2, branched or cyclic. Generally, the radicals R can be equipped with any type of substituent or substituents provided they do not interfere with any other constituents or substituents of the composition and do not interfere with the curing reaction.

The term "interfere" as used in the context of the present text relates to any influence of such a substituent on at least one of the other substituents or constituents of the composition or the curing reaction, or both, which might be detrimental to the properties of the hardened product.

The term "detrimental" as used in the context of the present text relates to a change of properties of the precursors or the cured product that negatively affect the usefulness of the precursors or the cured product in their intended use.

In another embodiment at least about 50% of the radicals R are methyl groups. Examples of other radicals R that can be present in the organopolysiloxanes according to the above formula are ethyl, propyl, isopropyl, n-butyl, tert.butyl, the pentyl isomers, the hexyl isomers, vinyl, propenyl, isopropenyl, 2- and 3-n-butenyl, the pentenyl isomers, the hexenyl isomers, fluorine substituted aliphatic radicals like 3,3,3-trifluoropropyl groups, cyclopentyl or cyclohexyl groups, cyclopentenyl or cyclohexenyl groups or aromatic or heteroaromatic groups like phenyl or substituted phenyl groups. Examples for such molecules are described in U.S. Pat. No. 4,035,453, the disclosure of which, especially regarding the above mentioned molecules, their chemical constitution and their preparation, is included herein by reference.

Particularly preferred are linear polydimethylsiloxanes according to the above formula having viscosities within the specified viscosity ranges and end groups comprising dimethylvinylsiloxy units and methyl groups as the radicals R.

A component (a) which can be employed can consist of one type (a1) of organopolysiloxane. The organopolysiloxane can have a viscosity starting in the range of 5 to 1,000,000 mPas, or 10 to 500,000 mPas or 20 to 50,000 or 30 to 40,000 mPas.

It is, however, also possible that component (a) comprises two or more constituents, (a1), (a2) and so on, which can differ, e.g., in the chemical composition of their backbone, or their molecular weight, or their substituents or their viscosity, or any other differentiating feature or two or more of the above mentioned features.

In one embodiment the difference in viscosities of different constituents of component (a) can be higher than a factor of 2, e.g., higher than a factor of 5, higher than a factor of 10, higher than a factor of 20, higher than a factor of 30, higher than a factor of 40, higher than a factor of 50, higher than a factor of 60, higher than a factor of 70, higher than a factor of 80, higher than a factor of 90 or higher than a factor of 100. The difference in viscosities can be even higher, e.g., higher than a factor of 200, higher than a factor of 300, higher than a factor of 500, higher than a factor of 800, higher than a factor of 1,000 or higher than a factor of 5,000, it should, however, preferably not exceed a value higher than a factor of 10,000. It should be kept in mind that the values mentioned above relate to a factor for the difference in viscosities, not the viscosity values themselves.

If component (a) contains constituents of different viscosities, the ratio of the amount of constituent with the lowest viscosity to the amount of constituent with the highest viscosity can be chosen relatively freely, depending on the desired properties of the precursors and the cured resin. It can, however, be advantageous when the ratio of the amount of constituent with the lowest viscosity to the amount of constituent with the highest viscosity is within a range of from 1:20 to 20:1, especially 1:10 to 10:1 or 1:5 to 5:1. Good results can e.g. be obtained with ratios of from 1:3 to 3:1 or 1:2 to 2:1. It can furthermore be adequate in some cases, when the amount of constituent with the highest viscosity is about equal to or higher than the amount of constituent with the lowest viscosity, resulting in a value of from 0.9:1 to 3:1 for the ratio of the amount of constituent with the highest viscosity to the amount of constituent with the lowest viscosity. All of the ratios are based on the weight of the constituents. According to another embodiment component (a) can be a QM resin containing vinyl groups.

QM resins comprise as Q a quadrifunctional $SiO_{4/2}$ unit and as M building blocks such as monofunctional units $R_3SiO_{1/2}$, wherein R is vinyl, methyl, ethyl or phenyl or tri- or bi-functional units.

A preferred QM resin which can be used as component (a) has the structure: $Si[O—Si(CH_3)_2—CH=CH_2]_4$.

Examples of suitable QM resins are e.g. described in US 2005/0027032. The content of this document with respect to the description of QM resins is herewith incorporated by reference.

QM resins can be used in addition to the organopolysiloxanes described above or instead of the organopolysiloxanes described above.

A component (a) which can be employed can consist of one type (a1) of organopolysiloxane.

The organopolysiloxane can have a viscosity starting in the range of 1 to 1,000,000 mPas, or 5 to 500,000 mPas or 10 to 50,000 or 30 to 40,000 mPas (at 23° C.).

The nature and structure of component (b) is not particularly limited unless the desired result cannot be achieved.

Component (b) acts as a crosslinker capable of crosslinking component (a).

Component (b) is typically an organohydrogenpolysiloxane with at least 3 SiH groups per molecule.

An organohydrogenpolysiloxane typically contains from about 0.01 to about 1.7 wt.-% silicon-bonded hydrogen or from 1.0 to 9.0 mmol SiH/g. The silicon valencies which are not saturated with hydrogen or oxygen atoms are typically saturated with monovalent hydrocarbon radicals R free from ethylenically unsaturated bonds.

The hydrocarbon radicals R, which may be selected independently from each other, represent a linear or branched or cyclic, non-substituted or substituted, aliphatic or aromatic monovalent hydrocarbon groups with 1 to 12 C atoms without ethylenically unsaturated bonds. In a preferred embodiment of the invention, at least 50%, preferably 100%, of the hydrocarbon radicals R that are bonded to silicon atoms are methyl radicals.

Organohydrogenpolysiloxanes which can be suitable include those having a viscosity of 10 to 1,000 mPas or from 15 to 550 mPas or from 20 to 250 mPas (at 23° C.).

Component (b) can be Present in the Following Amounts: Lower limit: at least 0.1 or at least 1 or at least 3 wt.-%; Upper limit: utmost 20 or utmost 15 or utmost 10 wt.-%; Range: from 0.1 to 20 or from 1 to 15 or from 3 to 10 wt.-%; wt.-% with respect to the weight of paste (A).

The nature and structure of component (c) is not particularly limited unless the desired result cannot be achieved.

Generally, as a component (c) all types of polyalkylsiloxanes having at least one carbinol, silanol, alkoxy, carboxy or amino group or a mixture of two or more of such groups can be employed as components (c). Using polyalkylsiloxanes having at least one silanol or alkoxy group are sometimes preferred.

It is generally possible that Paste (A) and/or Paste (B) contains a component (c) with only one constituent, namely a polydiorganosiloxane having at least one carbinol, silanol, alkoxy, carboxy or amino group.

It is, however, also possible that Paste (A) and/or Paste (B) contains an alkylsiloxane having at least one carbinol and at least one carboxy group or at least one carbinol and at least one amino group or at least one carboxy group and at least one amino group or at least one carbinol and at least one carboxy group and at least one amino group.

It is also possible that Paste (A) and/or Paste (B) contains at least one alkylsiloxane having at least one carbinol and at least one alkylsiloxane having at least one carboxy group or at least one alkylsiloxane having at least one carbinol group and at least one alkylsiloxane having at least one amino group or at least one alkylsiloxane having at least one carboxy group and at least one alkylsiloxane having at least one amino group or at least one alkylsiloxane having at least one carbinol group and at least one alkylsiloxane having at least one carboxy group and at least one alkylsiloxane having at least one amino group. Polydiorganosiloxane having at least one silanol group contain the structural moiety Si—OH.

An example of a suitable polysiloxane having two or more hydroxy groups includes polydialkylsiloxanes, for example polydimethylsiloxane, that are terminated with a hydroxy group at both opposite ends of the polymer chain. Generally, the hydroxyl terminated polydialkylsiloxanes will have a weight average molecular weight of about 900 to 500,000, for example between 1500 and 150,000 g/mol.

Suitable silane compounds having two or more hydrolysable groups include in particular esters of silic acid, esters of polysilic acid and polysiloxanes having two or more alkoxy groups bound to a silicium atom. Typical examples include compounds according to the formula:

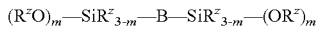

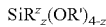

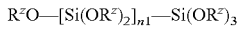

wherein in the above B represents the divalent group of formula —O—(SiR$_2$—O)$_{m2}$— with R representing an aromatic or aliphatic hydrocarbon group which may optionally be substituted and m2 represents a value of 10 to 6000, R' and R$^z$ independently represents an alkyl group or an aryl group that may be substituted, n1 represents a value of 1 to 100, m is an integer of 1 to 3 and z is 0, 1 or 2.

In a preferred embodiment of the present invention component (c) contains at least one component of the formula

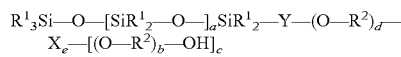 (II) or

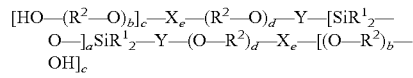 (III) or

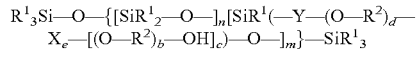 (IIIa) or (IIIb)

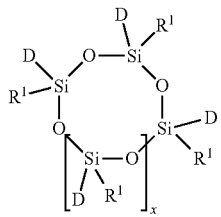

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, R$^1$ is a linear or branched alkyl or fluoroalkyl group with 1 to 8 C-atoms or a cycloalkyl or aryl group with 6 to 14 C-atoms, R$^2$ is a linear or branched alkylene group that may contain a carbonyl group with 1 to 8 C-atoms, D is R$^1$ or —Y—(O—R$^2$)$_d$—X$_e$—[(O—R$^2$)$_b$—OH]$_c$ with at least one residue —Y—(O—R$^2$)$_d$—X$_e$—[(O—R$^2$)$_b$—OH]$_c$ per molecule, 1≤a≤10.000, 0≤b≤500, 1≤c≤6, 0≤d≤500, e is 0 or 1, 0≤n≤500, 0≤m≤100 where m+n exceed 5 and x is 0, 1, 2, 3, 4, 5 or 6.

In another embodiment component (c) contains at least one component of the formula

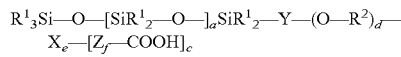 (IV) or

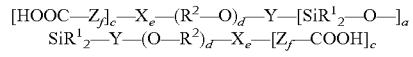 (V) or

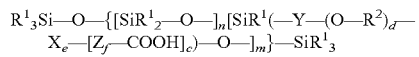 (Va) or (Vb)

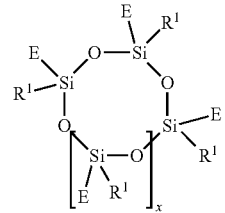

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, Z is a linear or branched alkylene or alkenylene or aryl group that may contain an ester group with 1 to 16 C-atoms, R$^1$ is a linear or branched alkyl or fluoroalkyl group with 1 to 8 C-atoms or a cycloalkyl or aryl group with 4 to 14 C-atoms, R$^2$ is a linear or branched alkylene group that may contain a carbonyl group with 1 to 8 C-atoms, E is R$^1$ or —Y—(O—R$^2$)$_d$—X$_e$—[Z$_f$—COOH]$_c$ with at least one residue —Y—(O—R$^2$)$_d$—X$_e$—[Z$_f$—COOH]$_c$ per molecule, 1≤a≤10.000, 1≤c≤6, 0≤d≤500, e is 0 or 1, f is 0 or 1, 0≤n≤500, 0≤m≤100 where m+n exceed 5 and x is 0, 1, 2, 3, 4, 5 or 6.

In another embodiment of the present invention component (c) contains at least one component of the following formulas:

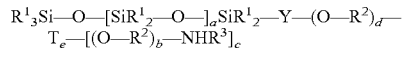 (VI) or

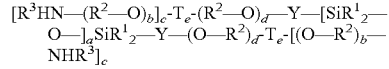 (VII) or

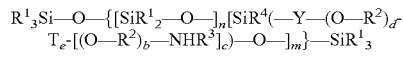 (VIIa) or (VIIb)

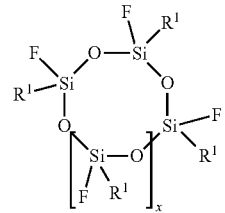

wherein T is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, R$^1$ is a linear or branched alkyl or fluoroalkyl group with 1 to 8 C-atoms or a cycloalkyl or aryl group with 6 to 14 C-atoms, R$^2$ is a linear or branched alkylene group that may contain a carbonyl group with 1 to 8 C-atoms, F is R$^1$ or —Y—(O—R$^2$)$_d$-T$_e$-[(O—R$^2$)$_b$—NHR$^3$]$_c$ with at least one residue —Y—(O—R$^2$)$_d$-T$_e$-[(O—R$^2$)$_b$—NHR$^3$]$_c$ per molecule, R$^3$ is a linear or branched alkyl or fluoroalkyl group with 1 to 8 C-atoms or a cycloalkyl or aryl group with 6 to 14 C-atoms or H, R$^4$ is R$^1$ or Methoxy or Ethoxy, 1≤a≤10.000, 0≤b≤10.000, 1≤c≤6, 0≤d≤500, e is 0 or 1, 0≤n≤500, 0≤m≤100 where m+n exceed 5 and x is 0, 1, 2, 3, 4, 5 or 6.

Preferred examples of the component (c) have the following structures:

(c1) Polydimethylsiloxanes with terminal or pendant carbinol groups. The polydimethylsiloxanes are preferably linear but can also be cyclic or T-shaped. A preferred structure is for example:

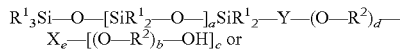

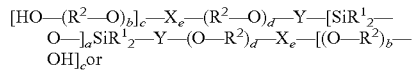

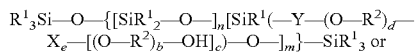

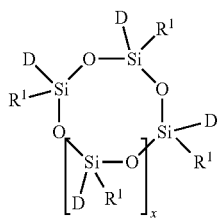

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, D is $R^1$ or —Y—(O—$R^2$)$_d$—X$_e$—[(O—$R^2$)$_b$—OH]$_c$ with at least one residue —Y—(O—$R^2$)$_d$—X$_e$—[(O—$R^2$)$_b$—OH]$_c$ per molecule, $1 \leq a \leq 10.000$, $0 \leq b \leq 500$, $1 \leq c \leq 6$, $0 \leq d \leq 500$, e is 0 or 1, $0 \leq n \leq 500$, $0 \leq m \leq 100$ where m+n exceed 5 and x is 0, 1, 2, 3, 4, 5 or 6.

Also preferred are:

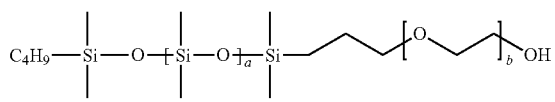

like MCR-C13 from Gelest company (CAS: 67674-67-3)

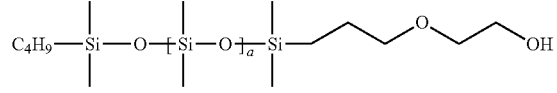

like MCR-C12 and MCR-C22 from Gelest company (CAS: 207308-30-3)

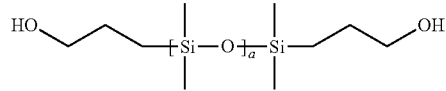

like Rhodorsil Oil 1647 V 60 and 1615 V 500 from Rhône-Poulenc (CAS: 58130-02-2)

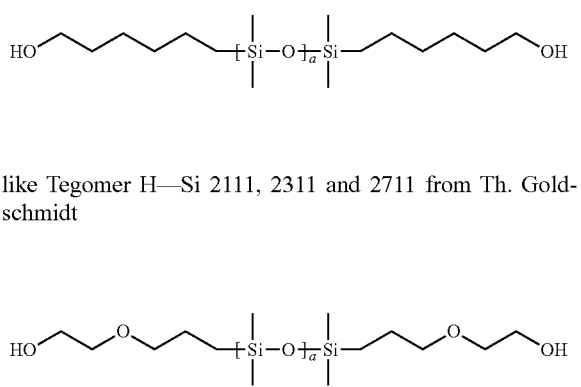

like Tegomer H—Si 2111, 2311 and 2711 from Th. Goldschmidt

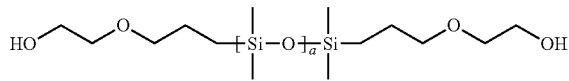

synthesized from allylglycol and Si—H terminated silicon oil

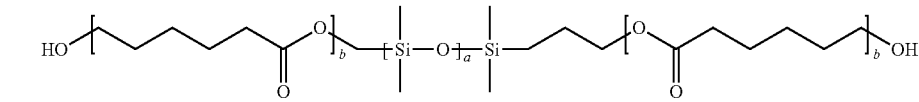

like DBL-C31 from Gelest company (CAS: 120359-07-1) or Tegomer H—Si 6440

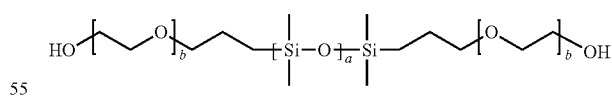

synthesized from allypolylglycol and Si—H terminated silicon oil according available from Hanse Chemie

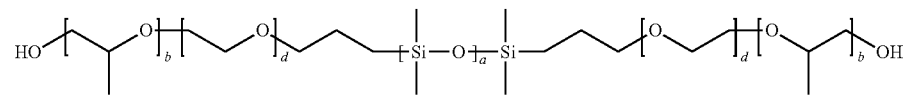

(EO+PO Adduct: Rhodorsil Oil 10646 from Rhône-Poulenc (CAS: 94469-32-6))

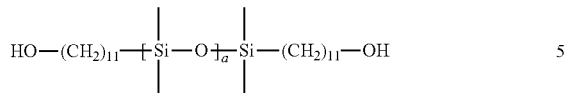

available from 10-undecene-1-ol and Si—H terminated silicon oil

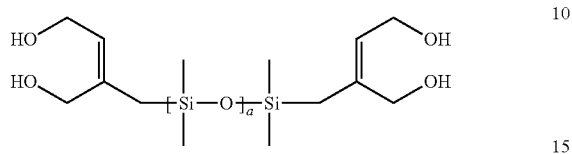

synthesized from 2-butin-1,4-diol and Si—H terminated silicon oil

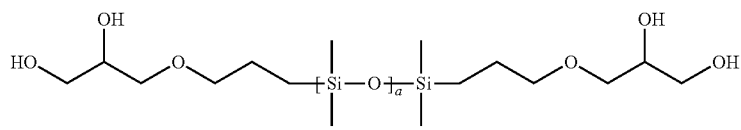

synthesized from Allylglycerol and Si—H terminated silicon oil, or from DMS-E01, E12 or E21 from Gelest company (CAS: 104780-61-2)

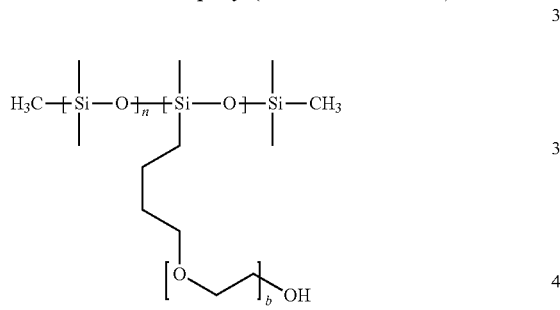

synthesized from Si—H pendant silicone oil and allyl polyglycole according to e.g. to U.S. Pat. No. 5,159,096,

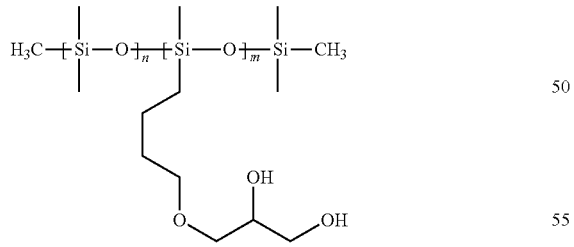

synthesized from Rhodorsil Oil 21620 from Rhône-Poulenc (CAS: 68440-71-1) and water

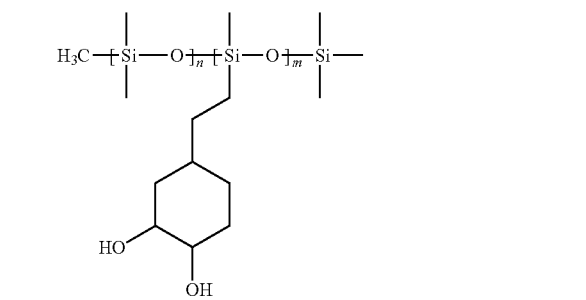

synthesized from VCHO and Si—H terminated silicon oil and addition of water synthesized from Silicorelease Poly 200 or RCA 200 from Rhône-Poulenc (CAS: 67762-95-2) and water

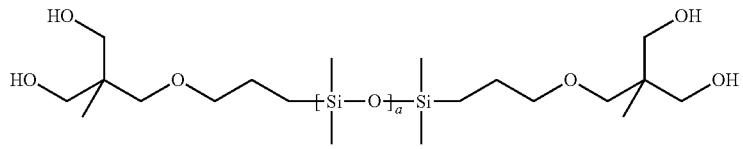

synthesized from trimethylolpropane-monoallyl ether and Si—H terminated silicon oil

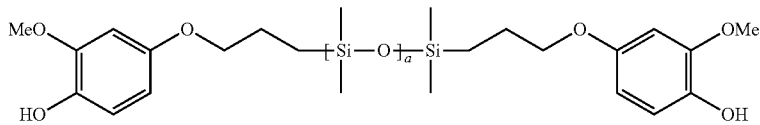

synthesized from eugenole and Si—H terminated silicon oil e.g. according to WO 97/03110 Example 4 or 5

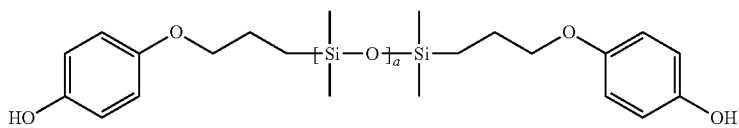

synthesized from allylphenole and Si—H terminated silicon oil, available from Shin Etsu Chemical Co., Ltd (Shih et al., J. Polym. Sci. 75 (2000) 545)

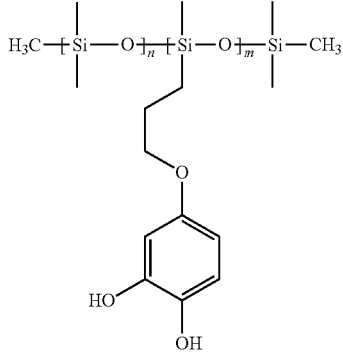

synthesized from eugenole and Si—H pendant silicon oil e.g. according to WO 97/03110 Example 1, 2 or 3

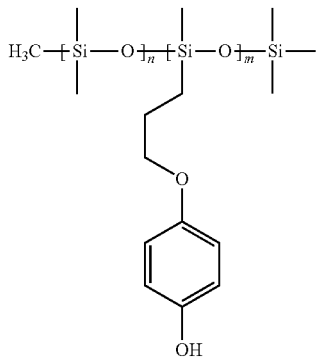

synthesized from allylphenole and Si—H pendant silicon oil

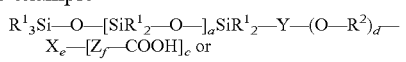

x: 4, 5, 6 synthesized from Si—H cyclics and allylglycol x: 4, 5, 6 synthesized from Si—H cyclics and eugenole

Especially preffered are also silicone oils with pendant carbinol groups like e.g. Silwet L-7200, L-7210, L-7220, L7230, L-7604, L-7644 or L-7657 of OSi.

(c2) Polydimethylsiloxanes with terminal or pendant carboxy groups. The polydimethylsiloxanes are preferably linear but can also be cyclic or T-shaped. A preferred structure is for example $R^1_3Si-O-[SiR^1_2-O-]_aSiR^1_2-Y-(O-R^2)_d-$
$X_e-[Z_f-COOH]_c$ or

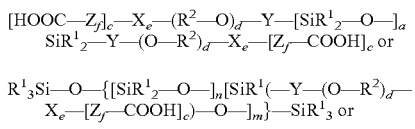

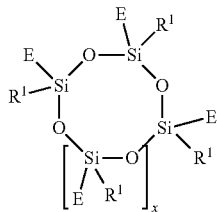

wherein X is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, Z is a linear or branched alkylene or alkenylene or aryl group that may contain an ester group with 1 to 16 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, E is $R^1$ or $—Y—(O—R^2)_d—X_e—[Z_f—COOH]_c$ with at least one residue $—Y—(O—R^2)_d—X_e—[Z_f—COOH]_c$ per molecule, 1≤a≤10.000, 1≤c≤6, 0≤d≤500, e is 0 or 1, f is 0 or 1, 0≤n≤500, 0≤m≤100 where m+n exceed 5 and x is 0, 1, 2, 3, 4, 5 or 6.

Also preferred are:

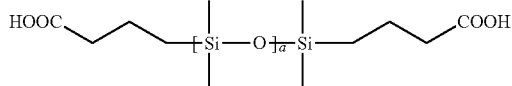

like DMS-B31 from Gelest company

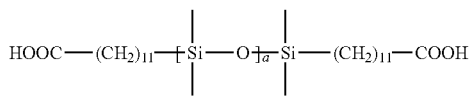

like DMS-B12 or B25 from Gelest company

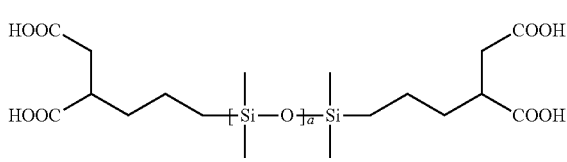

like DMS-Z11 from Gelest company and the corresponding acid

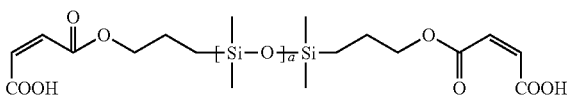

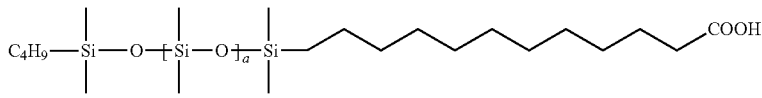

like MCR-B11 or CR—B16 from Gelest company synthesized from carbinol terminated silicones and maleic anhydride

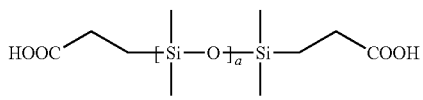

synthesized from methyl acrylate and Si—H terminated silicon oil and following saponification

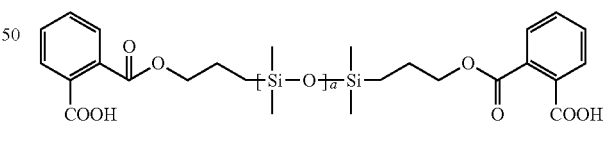

synthesized from carbinol terminated silicones and phthalic anhydride

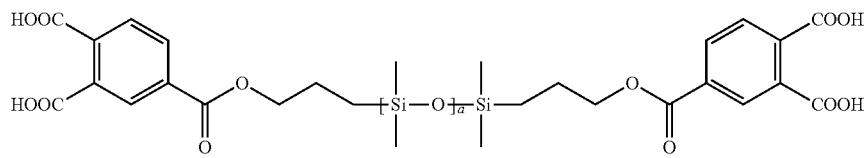

synthesized from carbinol terminated silicones and trimellitic anhydride chloride

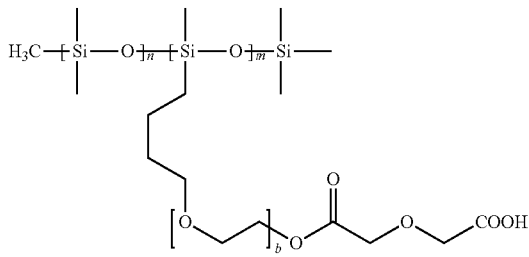

from carbinol pedant silicones and glycolic acid anhydride

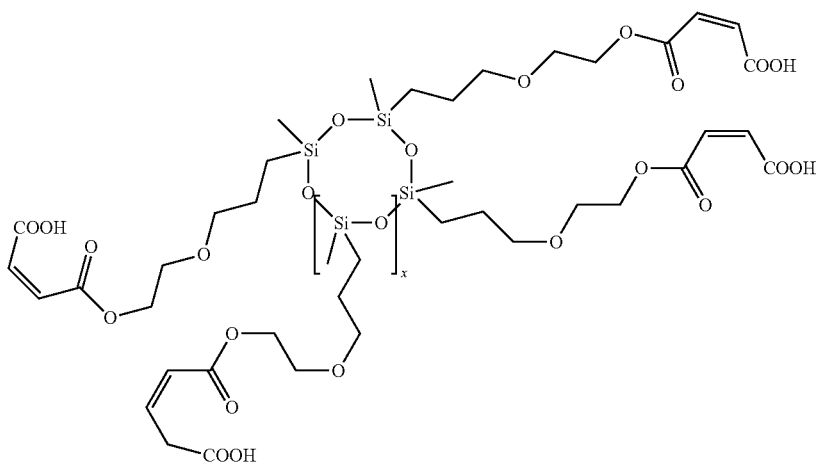

synthesized from Si—H cyclics allyl glycol and subsequent reaction with maleic anhydride (c3) Polydimethylsiloxanes with terminal or pendant amino groups. The polydimethylsiloxanes are preferably linear but can also be cyclic or T-shaped. A preferred structure is for example

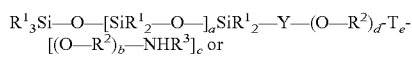

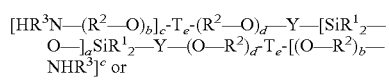

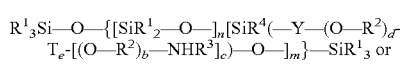

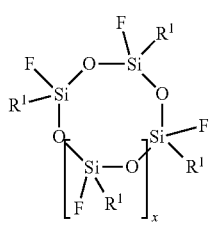

wherein T is a linear or branched hydrocarbon or an aryl residue that may contain an oxygen atom and/or an ether group with 6 to 14 C-atoms and a valency of c, Y is a linear or branched alkylene group with 1 to 10 C-atoms or a cycloalkyl group with 4 to 14 C-atoms, $R^1$ is a linear or branched alkyl or fluoroalkyl group with 1 to 8 C-atoms or a cycloalkyl or aryl group with 6 to 14 C-atoms, $R^2$ is a linear or branched alkylene group that may contain a carbonyl group with 1 to 8 C-atoms, F is $R^1$ or —Y—(O—$R^2$)$_d$-T$_e$-[(O—$R^2$)$_b$—NHR$^3$]$_c$ with at least one residue —Y—(O—$R^2$)$_d$-T$_e$-[(O—$R^2$)$_b$—NHR$^3$]$_c$ per molecule, $R^3$ is a linear or branched alkyl or fluoroalkyl group with 1 to 8 C-atoms or a cycloalkyl or aryl group with 6 to 14 C-atoms or H $R^4$ is $R^1$ or Methoxy or Ethoxy, $1 \leq a \leq 10.000$, $0 \leq b \leq 500$, $1 \leq c \leq 6$, $0 \leq d \leq 500$, e is 0 or 1, $0 \leq n \leq 500$, $0 \leq m \leq 100$ where m+n exeed 5 and x is 0, 1, 2, 3, 4, 5 or 6.

Also preferred are:

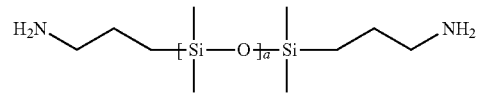

like PDMS Diamine 5 k, 10 k or 15 k from 3M or Tegomer A-Si 2120 or 2130 from Th. Goldschmidt or DMS-A11, A12, A15, A25 or A32 from Gelest company (CAS: 106214-84-0)

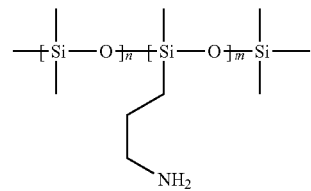

like Rhodorsil 21643 and 21644 from Rhône-Poulenc or AMS-132, 152, and 162 from Gelest company (CAS: 99363-37-8)

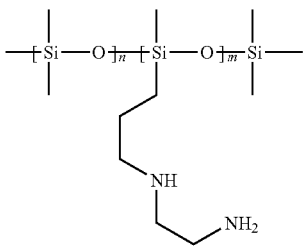

like Rhodorsil 21642 and 21637 from Rhône-Poulenc (CAS: 102782-92-3) or AMS-232 from Gelest company (CAS: 71750-79-3)

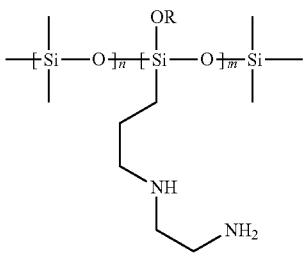

like Belsil ADM-Types of Wacker or ATM-1112 or 1322 from Gelest company,

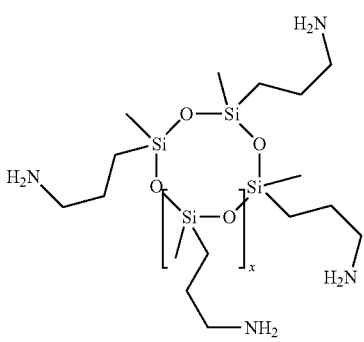

synthesized from Si—H cyclics acrylonitrile and subsequent reaction with LiAlH4.

According to one embodiment, Paste (A) contains the components in the following amounts:
polyorganosiloxane with at least two olefinically unsaturated groups: from 10 to 60 or from 15 to 45 wt.-%;
organohydrogenpolysiloxane: from 0.1 to 20 or from 1 to 15 wt.-%;
alkylsiloxane having at least one carbinol, carboxyl or amino group and/or at least one alkylsiloxane having at least one silanol group: from 0 to 25 or from 2 to 16 wt.-%;
filler(s): from 0 to 75 or from 1 to 60 wt.-%;
additive(s): from 0 to 15 or from 0.5 to 10 wt.-%;
wt.-% with respect to the weight of Paste (A).

In certain embodiments Paste (B) has a consistency according to ISO 4823 in the range from 25 to 50 mm.

Paste (B) comprises
at least one polyorganosiloxane, optionally with aliphatically unsaturated groups as component (d),
at least one addition cure catalyst as component (e), and
optionally at least one alkylsiloxane having at least one carbinol, carboxyl or amino group or at least one alkylsiloxane having at least one silanol group as component (c),
optionally filler(s) as component (h),
optionally additive(s) as component (i).

The nature and structure of component (d) is not particularly limited unless the desired result cannot be achieved.

Paste (B) contains organopolysiloxanes with or without reactive substituents.

If reactive substituents are present, those are typically aliphatically unsaturated groups. In this case, the polyorganosiloxane according to component (d) is identical to the polyorganosiloxane according to component (a).

Non-reactive substituents include those which do not co-polymerize with the other components of the composition during the hardening process. These are preferably linear, branched or cyclic organopolysiloxanes where all silicon atoms are surrounded by oxygen atoms or monovalent hydrocarbon radicals with 1 to 18 carbon atoms which can be substituted or non-substituted. The hydrocarbon radicals can be methyl, ethyl, $C_2$-$C_{10}$ aliphatics, trifluoropropyl groups as well as aromatic $C_6$-$C_{12}$ radicals.

Polydimethylsiloxanes with trimethylsiloxy end groups can be preferred and can be used in an amount of 0 to 40 wt.-%, or 0.1 to 20 wt.-% or 0.5 to 10 wt.-% with respect to the whole composition.

The nature and structure of component (e) is not particularly limited unless the desired result cannot be achieved.

The addition cure catalyst is typically a platinum catalyst or a platinum containing catalyst, including a platinum complex which can be prepared from hexachloroplatinum acid by reduction with tetramethyldivinyldisiloxane. Such compounds are known to the skilled person.

Any other compounds which catalyze or accelerate addition cross-linking of silanes with ethylenically unsaturated double bonds are also suitable. Platinum-siloxane complexes as described, e.g. in U.S. Pat. Nos. 3,715,334, 3,775,352 and 3,814,730 are suitable. The disclosure of these patents with regard to platinum complexes and their preparation is explicitly mentioned and expressly regarded as part of the disclosure of the present text.

If the catalyst is a Pt containing catalyst, the catalyst component (C) may be present in the following amounts:
Lower amount: at least 0.00005 or at least 0.0002 wt.-%;
Upper amount: utmost 0.05 or utmost 0.04 wt.-%;
Range: from 0.00005 to 0.05 or from 0.0002 to 0.04 wt.-%, calculated as elemental platinum and related to the weight of paste (B).

According to one embodiment, Paste (B) contains the components in the following amounts:
polyorganosiloxane optionally comprising olefinically unsaturated groups: from 10 to 60 or from 15 to 45 wt.-%;
Pt containing addition cure catalyst: from 0.00005 to 0.05 or from 0.0002 to 0.04 wt.-%, if calculated as elemental platinum;
alkylsiloxane having at least one carbinol, carboxyl or amino group/or at least one alkylsiloxane haven at least one silanol group: from 0 to 25 or from 1 to 16 wt.-%;
filler(s): from 0 to 75 or from 1 to 60 wt.-%;
additive(s): from 0 to 15 or from 1 to 10 wt.-%;
wt. % with respect to the weight of Paste (B).

In certain embodiments Paste (C) fulfils at least one or more, sometimes all of the following parameters:
having a consistency according to ISO 4823 in the range from 25 to 50 mm;

having a colour different than Paste (A) or Paste (B) or a mixture of Paste (A) and Paste (B).

Paste (C) comprises
a softener as component (f),
a condensation cure catalyst as component (g),
optionally filler(s) as component (h),
optionally additive(s) as component (i), and
optionally polyorganosiloxane optionally comprising olefinically unsaturated groups.

The nature and structure of component (f) is not particularly limited unless the desired result cannot be achieved.

Specific examples for the softener according to component (f) include mineral oil, paraffin, vaseline and mixtures thereof.

The nature and structure of the condensation cure catalyst according to component (g) is not particularly limited unless the desired result cannot be achieved.

Examples of condensation cure catalyst (g) include aluminum alkoxides, antimony alkoxides, barium alkoxides, boron alkoxides, calcium alkoxides, cerium alkoxides, erbium alkoxides, gallium alkoxides, silicon alkoxides, germanium alkoxides, hafnium alkoxides, indium alkoxides, iron alkoxides, lanthanum alkoxides, magnesium alkoxides, neodymium alkoxides, samarium alkoxides, strontium alkoxides, tantalum alkoxides, titanium alkoxides, tin alkoxides, vanadium alkoxide oxides, yttrium alkoxides, zinc alkoxides, zirconium alkoxides, titanium or zirconium compounds, especially titanium and zirconium alkoxides, and chelates and oligo- and polycondensates of the above alkoxides, dialkyltin diacetate, tin(II)octoate, dialkyltin diacylate, dialkyltin oxide and double metal alkoxides. Double metal alkoxides are alkoxides containing two different metals in a particular ratio. In particular, the following are employed: titanium tetraethylate, titanium tetrapropylate, titanium tetraisopropylate, titanium tetrabutylate, titanium tetraisooctylate, titanium isopropylate tristearoylate, titanium triisopropylate stearoylate, titanium diisopropylate distearoylate, zirconium tetrapropylate, zirconium tetraisopropylate, zirconium tetrabutylate. In addition, titanates, zirconates and hafnates as described in DE 4427528 C2 and EP 0 639 622 B1 can be used.

According to one embodiment, Paste (C) contains the components in the following amounts:
a softener: from 5 to 95 or from 10 to 75 wt.-%;
a condensation cure catalyst: from 0.1 to 15 or from 1 to 10 wt.-%;
optionally filler(s): from 0 to 70 or from 1 to 60 wt.-%;
optionally additive(s): from 0 to 15 or from 1 to 10 wt.-%.
optionally polyorganosiloxane optionally comprising aliphatically unsaturated groups: from 0 to 30 or from 1 to 25 wt.-%;
wt.-% with respect to the weight of Paste (C).

Either of the pastes or compositions described in the present text may contain filler(s) as component (h), in particular an inorganic filler.

The chemical nature and structure of the filler(s) is not particularly limited unless it is contra productive for achieving the intended result.

According to one embodiment, the paste(s) described in the present text comprise reinforcing filler(s) as component (h1).

The filler (h1) may be described by the following feature: having a BET surface of at least 50 m$^2$/g, e.g. from 50 to 400 m$^2$/g. If desired, the BET surface of the filler can be determined as described in DIN 66132.

Suitable filler(s) (h1) include pyrogenic or fumed or precipitated silicic acid. Those filler are commercially available from companies like Wacker or Degussa under the trade names Aerosil™, Sipernat™, HDK-H™ or Aeroxide™.

The surface of the filler (h1) may be surface treated, e.g. by treatment with organosilanes or siloxanes or by the etherification of hydroxyl groups to alkoxy groups.

The surface treatment can be carried out, e.g. with dimethyldichlorosilane, hexamethyldisilazane, tetramethylcyclotetrasiloxane or polymethylsiloxane.

If present, filler (h1) may be present in the following amounts:
Lower amount: at least 0.1 or at least 0.5 or at least 1 wt.-%;
Upper amount: utmost 50 or utmost 20 or utmost 10 wt.-%;
Range: from 0.1 to 50 or from 0.5 to 20 or from 1 to 10 wt.-%;
wt.-% with respect to the weight of the respective Paste (A), Paste (B) or Paste (C).

If the amount of the filler (h1) is too high, the consistency and rheological properties of the pastes will not be adequate for an impression material to capture good detail accuracy of the preparation margins and teeth in a patient's mouth.

If the amount of the filler (h1) is too low, the strengthening effect may be too low and separation effects in the paste may occur, e.g. sedimentation of fillers.

According to one embodiment, the paste(s) described in the present text comprise non-reinforcing filler(s) as component (h2).

Inorganic filler (h2) may be described by the following features:
maximum particles size: 200 μm or below; or 150 μm or below;
BET surface: below 50 m$^2$/g; or from 1 to 40 m$^2$/g.

Examples for the inorganic filler component (h2) include quartz, cristobalitee, calcium silicate, diatomaceous earth, zirconium silicate, montmorillonite such as bentonite, zeolite, including molecular sieves such as sodium aluminium silicate, metal oxide powder such as aluminium oxide, titanium oxide or zinc oxide or their mixed oxides, barium sulphate, calcium carbonate, plaster, glass and mixtures thereof.

If desired, the inorganic filler component (h2) can be surface-treated, as well. The surface treatment can generally be carried out with the same methods as described in the case of inorganic filler component (h1).

If present, filler (h2) may be present in the following amounts:
Lower amount: at least 0.1 or at least 1 or at least 10 wt.-%;
Upper amount: utmost 80 or utmost 75 or utmost 70 wt.-%;
Range: from 0.1 to 80 or from 1 to 75 or from 10 to 70 wt.-%;
wt.-% with respect to the weight of Paste (A), Paste (B) or Paste (C).

If the amount of filler (h2) is too high, hardness of the set impression will become too high so that it can become difficult to remove it from a patient's mouth.

If the amount of the filler (h2) is too low, the required hardness of the set impression to be able to pour it with gypsum without distortions may not be achieved.

Using a combination of reinforcing filler (h1) and non-reinforcing fillers (h2) can be preferred. In this respect, the quantity of reinforcing fillers (h1) can range from 0.1 to 10 wt.-%, in particular from 0.4 to 8 wt.-% with respect to the respective Paste (A), Paste (B) or Paste (C).

Either of the pastes or compositions described in the present text may contain additive(s) as component (i).

The chemical nature and structure of the additive(s) is not particularly limited unless it is contra productive for achieving the intended result.

Those additives include hydrophilating agent(s), retarder(s) to modify the working and setting time (e.g. 3-methyl-1-butyne-3-ol or 1,1,3,3-tetramethyl-1,3-divinyl siloxane (VMO)), inhibitor(s), colourant(s) (i.e. pigment(s) and dye(s)), stabilizer(s), flavouring(s), hydrogen scavenger(s), rheology modifier(s) (e.g. synthetic or natural waxes or polyethylene/propylene diacetats as described in EP 1 165 016 A1; corresponding to U.S. Pat. No. 6,677,393) etc. alone or in admixture.

To control the reactivity of the addition reaction and to prevent premature curing, it may be advantageous to add an inhibitor, which prevents the addition reaction for a specific period of time or slows the addition reaction down. Such inhibitors are known and described, e.g. in U.S. Pat. No. 3,933,880. This content of this reference regarding such inhibitors and their preparation is expressly regarded as being part of the disclosure of the invention and herewith incorporated by reference.

Examples of such inhibitors include acetylenic unsaturated alcohols such as 3-methyl-1-butyne-3-ol, 1-ethynylcyclohexane-1-ol, 3,5-dimethyl-1-hexyne-3-ol and 3-methyl-1-pentyne-3-ol. Examples of inhibitors based on vinyl siloxane are 1,1,3,3-tetramethyl-1,3-divinyl siloxane, 1,3,5,7-tetravinyl-1,3,5,7-tetramethylcyclotetrasiloxane and poly-, oligo- and disiloxanes containing vinyl groups.

The paste(s) may also contain a component useful for diminishing the presence or degree of hydrogen outgassing which may be typically generated as a result of the vinyl polymerization in the case of SiH curable composition. The composition thus may comprise a hydrogen scavenger such as finely divided platinum metal that scavenges for and takes up such hydrogen. The Pt metal may be deposited upon a substantially insoluble salt having a surface area of between about 0.1 and about 40 m²/g. Suitable salts are Barium sulphate, barium carbonate and calcium carbonate of suitable particle sizes. Other substrates include diatomaceous earth, activated alumina, activated carbon and others. The inorganic salts are especially preferred to imply improved stability to the resulting materials incorporating them. Dispersed upon the salts is 0.2 to 2 parts per million of platinum metal, based upon the weight of the catalyst component. It has been found that employment of the platinum metal dispersed upon inorganic salt particles substantially eliminates or diminishes hydrogen outgassing during curing of dental silicones. Also Pd metal (e.g. as described e.g. in U.S. Pat. No. 4,273,902) or Pd compounds (e.g. as disclosed in to U.S. Pat. No. 5,684,060) can be employed.

The paste(s) may further contain a stabilizer as component, e.g. selected from antioxidants and mixtures thereof.

Useful antioxidant(s) which can be used include: Vitamin E; N,N'-di-2-butyl-1,4-phenylenediamine; N,N'-di-2-butyl-1,4-phenylenediamine; 2,6-di-tert-butyl-4-methylphenol; 2,4-dimethyl-6-tert-butylphenol; 2,4-dimethyl-6-tert-butylphenol and 2,6-di-tert-butyl-4-methylphenol; 2,6-di-tert-butylphenol; Pentaerythritoltetrakis(3-(3,5-di-tert-butyl-4-hydroxyphenyl)propionate) (Irganox™ 1010); Octyl-3,5-di-tert-butyl-4-hydroxy-hydrocinnamate; Octadecyl 3-(3,5-di-tert-butyl-4-hydroxyphenyl)propionate; 1,3,5-Trimethyl-2,4,6-tris(3,5-di-tert-butyl-4-hydroxybenzyl)benzene; 2,2',4,4'-Tetrakis-tert-butyl-3,3-dihydroxybiphenyl; 4,4-Butylidenebis(6-tert-butyl-m-cresol); 4,4'-Isopropylidenbis-(2-tert-butylphenol); 2,2'-methylenebis(6-nonyl-p-cresol); 1,3,5-tris(3,5-di-tert-butyl-4-hydroxybenzyl-)-1,3,5-triazine-2,4,6(1H,3H,5H)trione; or mixtures thereof. Particularly useful include antioxidants comprising a phenolic moiety, especially a sterically hindered phenolic moiety.

Other stabilizers which can be used include stabilizers containing a phosphorous moiety, like organo phosphines, organo-phosphites, organo-phosphonites, di(organo-phoshites, di(organo-phosphonites) and mixtures thereof. A more detailed description of those stabilizers is given on page 16, line 30 to page 18, line 15 of WO 2007/001869 A2. The content of WO 2007/001869 with respect to these stabilizers is herewith incorporated by reference.

The paste(s) may also contain at least one hydrophilizing agent.

Surfactants or hydrophilizing agents which can be employed can generally be chosen freely from all types of surfactants which improve the hydrophilicity of a silicone moiety containing material (especially, if curable via a hydrosilylation reaction).

Useful surfactants can generally be chosen from anionic, cationic or non-ionic surfactants or mixtures of two or more of such types of surfactants.

It can be preferred, if the hardenable composition comprises a non-ionic surfactant as a hydrophilizing agent or a mixture of two or more non-ionic surfactants.

Ethoxylated fatty alcohols can be used. Suitable examples are e.g. described in EP 0 480 238 B1.

Also preferred are non-ionic surface-active substances including nonylphenolethoxylates, polyethylene glycolmono- and diesters, sorbitan esters and polyethylene glycolmono- and diethers. Suitable examples are described e.g. in U.S. Pat. No. 4,782,101. The content of these documents with regard to hydrophilizing agents and their preparation is herewith incorporated by reference.

Suitable hydrophilizing agents also include wetting agents from the group of hydrophilic silicone oils, which are not capable of being covalently incorporated into the hardened polymer network. Suitable hydrophilizing agents are described e.g. in U.S. Pat. No. 4,657,959 and in EP 0 231 420 B1. The content of these documents with regard to hydrophilizing agents and their preparation is herewith incorporated by reference.

Suitable silicone moieties containing surfactants can be summarized under the following formula

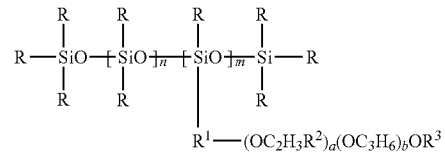

where each R is independently a monovalent hydrocarbyl radical with 1 to 22 C-atoms, $R^1$ is a divalent hydrocarbylene radical 1 to 26 C-atoms, each $R^2$ is independently hydrogen or a lower hydroxyalkyl radical, $R^3$ is hydrogen or a monovalent hydrocarbyl radical with 1 to 22 C-atoms, n and b are independently greater than or equal to zero, and m and a are independently greater than or equal to one, with the proviso that a has a sufficient value and b is small enough so that a cured composition of the invention has the desired water contact angle.

Preferably R and $R^3$ are —$CH_3$, $R^1$ is —$C_3H_6$—, $R^2$ is hydrogen, n is about zero or about one, m is about one to about five, a is about five to about 20 and b is about 0.

Several of such ethoxylated surfactants are for example available from Momentive Performance Materials Inc. including "Silwet™" surface active copolymers. Preferred surface active copolymers include Silwet 35, Silwet L-77, Silwet L-7600 and Silwet L-7602, Silwet L-7608 and Silwet Hydrostable 68 and Silwet Hydrostable 611. Silwet L-77 is an especially preferred ethoxylated surfactant which is believed to correspond to the above formula where R and $R^3$ are —$CH_3$, $R^1$ is —$C_3H_6$—, $R^2$ is hydrogen, n is about zero or about one, m is about one or about two, a is about seven, and b is about 0. Also possible is the use of MASIL™ SF19, as obtainable from Lubrizol performance products, Spartanburg, US.

Useful surfactants also include polyether carbosilanes of the general formula Q-P—$(OC_nH_{2n})_x$—OT, in which Q stands for $R_3$—Si— or $R_3$—(R'—$SiR_2$)$_a$—R'—$SiR''_2$— where every R in the molecule can be the same or different and stands for an aliphatic $C_1$-$C_{18}$, a cycloaliphatic $C_6$-$C_{12}$ or an aromatic $C_6$-$C_{12}$ hydrocarbon radical, which can optionally be substituted by halogen atoms, R' is a $C_1$-$C_{14}$ alkylene group, R" is R in the case of a≠0 or is R or $R_3$SiR' in the case of a=0, and a=0-2; P stands for a $C_2$-$C_{18}$ alkylene group, preferably a $C_2$-$C_{14}$ alkylene group or A-R''', where A represents a $C_2$-$C_{18}$ alkylene group and R''' a functional group from the following list: —NHC(O)—, —NHC(O)—(CH2)$_{n-1}$—, —NHC(O)C(O)—, —NHC(O)(CH2)$_v$C(O)—, —OC(O)—, —OC(O)—(CH2)$_{n-1}$—, —OC(O)C(O)—, —OC(O)(CH$_2$)$_v$C(O)—, —OCH$_2$CH(OH)CH$_2$OC(O)(CH2)$_{n-1}$—, —OCH$_2$CH(OH)CH$_2$OC(O)(CH2)$_v$C(O)— with v=1-12; T is H or stands for a $C_1$-$C_4$ alkyl radical or a $C_1$-$C_4$ acyl radical; x stands for a number from 1 to 200 and n stands for an average number from 1 to 6, preferably 1 to 4. Thus, the element —$SiR''_2$-can also comprise the substructure —Si(R)(R$_3$SiR')—.

The polyether part can be a homopolymer, but can also be a statistical, alternating or block copolymer.

Suitable polyether carbosilanes are selected from the group consisting of:
Et$_3$Si—(CH$_2$)$_3$—O—(C$_2$H$_4$O)y-CH$_3$, Et=Ethyl; Et$_3$Si—CH$_2$—CH$_2$—O—(C$_2$H$_4$O)y-CH$_3$, Et=Ethyl; (Me$_3$Si—CH$_2$)$_3$ Si—(CH$_2$)$_3$—O—(C$_2$H$_4$O)y-CH$_3$, Me=Methyl; Me$_3$Si—CH$_2$—SiMe$_2$-(CH$_2$)$_3$—O—(C$_2$H$_4$O)y-CH$_3$, Me=Methyl; (Me$_3$Si—CH$_2$)$_2$SiMe-(CH$_2$)$_3$—O—(C$_2$H$_4$O)y-CH$_3$, Me=Methyl; Me$_3$Si—(CH$_2$)$_3$—O—(C$_2$H$_4$O)y-CH$_3$, Me=Methyl; Me$_3$Si—CH$_2$—CH$_2$—O—(C$_2$H$_4$O)y-CH$_3$, Me=Methyl; Ph$_3$Si—(CH$_2$)$_3$—O—(C$_2$H$_4$O)y-CH$_3$, Ph=phenyl; Ph$_3$Si—CH$_2$—CH$_2$—O—(C$_2$H$_4$O)y-CH$_3$, Ph=phenyl; Cy$_3$Si—(CH$_2$)$_3$—O—(C$_2$H$_4$O)y-CH$_3$, Cy=cyclohexyl; Cy$_3$Si—CH$_2$—CH$_2$—O—(C$_2$H$_4$O)y-CH$_3$, Cy=cyclohexyl; (C$_6$H$_{13}$)$_3$Si—(CH$_2$)$_3$—O—(C$_2$H$_4$O)y-CH$_3$, (C$_6$H$_{13}$)$_3$Si—CH$_2$—CH$_2$—O—(C$_4$H$_4$O)y-CH$_3$ in which y conforms to the relation: 5≤y≤20 and mixtures thereof.

Surfactants which can also be used, either alone or as a mixture of two or more thereof, can be found in U.S. Pat. No. 5,750,589 (Zech et al), col. 2, l. 47 to col. 3 l. 27 and col. 3, l. 49 to col. 4, l. 4 and col. 5, l. 7 to col. 14, l. 20.

Other surfactants which can be used, either alone or as a mixture of two or more thereof, can be found in U.S. Pat. No. 4,657,959 (Bryan et al.), col. 4, l. 46 to col. 6. l. 52 as well as in EP 0 231 420 B1 (Gribi et al.) p4, l. 1 to p. 5, l. 16 and in the examples.

The content of these documents with regard to hydrophilizing agents and their preparation is herewith incorporated by reference.

In a particular embodiment, a mixture of a silicone moieties containing surfactant and one or more non-ionic surfactants selected from alkoxylated hydrocarbon surfactants is used. Examples of useful non-ionic surfactants include those according to the formula:

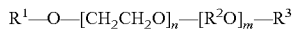
$R^1$—O—[CH$_2$CH$_2$O]$_n$—[R$^2$O]$_m$—R$^3$ wherein $R^1$ represents an aromatic or aliphatic, linear or branched hydrocarbon group having at least 8 carbon atoms, $R^2$ represents an alkylene having 3 carbon atoms, $R^3$ represents hydrogen or a C1-C3 alkyl group, n has a value of 0 to 40, m has a value of 0 to 40 and the sum of n+m being at least 2.

It will be understood that in the above formula, the units indexed by n and m may appear as blocks or they may be present in an alternating or random configuration. Examples of non-ionic surfactants according to the formula above include alkylphenol oxethylates such as ethoxylated p-isooctylphenol commercially available under the brand name TRITON™ such as for example TRITON™ X 100 wherein the number of ethoxy units is about 10 or TRITON™ X 114 wherein the number of ethoxy units is about 7 to 8. Still further examples include those in which $R^1$ in the above formula represents an alkyl group of 4 to 20 carbon atoms, m is 0 and $R^3$ is hydrogen. An example thereof includes isotridecanol ethoxylated with about 8 ethoxy groups and which is commercially available as GENAPOL®X080 from Clariant GmbH. Non-ionic surfactants according to the above formula in which the hydrophilic part comprises a block-copolymer of ethoxy groups and propoxy groups may be used as well. Such non-ionic surfactants are commercially available from Clariant GmbH under the trade designation GENAPOL® PF 40 and GENAPOL® PF 80. Further suitable non-ionic surfactants that are commercially available include Tergitol™ TMN 6, Tergitol™ TMN 10, or Tergitol™ TMN 100X. Also statistical, alternating or block copolymers of ethylene oxide and propylene oxide are suitable surfactants according to the present invention. Such non-ionic surfactants are available e.g. under the trade name Breox™ A, Synperonic™ or Pluronic™.

Besides or in addition to the hydrophilazing agent(s) described above, the composition may comprise any of the following components:
ethylene oxide or propylene oxide polymers or ethylene-propylene block polymers bearing as end groups polymerizable moieties selected from vinly, allyl, —OCO—(CH$_3$)C=CH$_2$;
H$_3$C—CO—[CH$_2$—CH$_2$—O—]$_m$—[CH$_2$—CH$_2$—CH$_2$—O—]$_n$—CO—CH$_3$ with n,m=10 to 100.

In addition to the hydrophilazing agent(s) mentioned above, the composition may also comprise one or more F-containing component as hydrophilating agent.

Suitable examples of the F-containing compound include:

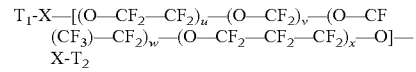
T$_1$-X—[(O—CF$_2$—CF$_2$)$_u$—(O—CF$_2$)$_v$—(O—CF(CF$_3$)—CF$_2$)$_w$—(O—CF$_2$—CF$_2$—CF$_2$)$_x$—O]—X-T$_2$ with u=0 to 8, v=0 to 8, w=0 to 14 and x=0 to 8 and u+v+w+x≥1, wherein $T_1$ and $T_2$ can be equal or different and are independently selected from the group consisting of —COOR, —CONR$^b$R$^c$—CH$_2$OH, —CF$_2$OR, —CHFOH, —CHFOR, —CH$_2$OR or —F with R and being a linear or branched alkyl rest (C1 to C9), aryl rest (C1 to C9) or alkylaryl rest (C1 to C9) each of which may optionally be substituted with one or more substituents selected from the group consisting of hydroxyl, amino group, halogen atom, an SiH group and a group capable of reacting with SiH, $R^b$ and $R^c$ independently representing H or having a meaning as given for R, and wherein X is selected from (CF$_2$)$_{1-6}$, CF(CF$_3$) and CHF—CF$_2$.

More precisely, the F-containing component can also be characterized by any of the following formulas:

Rf—(O)$_t$—CHF—(CF$_2$)$_x$-T, with t=0 or 1, x=0 or 1 and Rf being a linear or branched per- or partly fluorinated alkyl rest (including C1 to C6 or C1 to C4), wherein the alkyl chain can be interrupted by O atoms, with the proviso that when t is 0, the Rf group is a linear or branched per- or partly fluorinated alkyl rest (including C1 to C6 or C1 to C4) interrupted by one or more O atoms, Rf—(OCF$_2$)$_m$—O—CF$_2$-T, with m=1 to about 6 and Rf being a linear or branched per- or partly fluorinated alkyl rest (including C1 to C6 or C1 to C4), wherein the alkyl chain can be interrupted by O atoms, CF$_3$—(CF$_2$)$_2$—(OCF(CF$_3$)—CF$_2$)$_z$—O-L-T, with z=0, 1, 2, 3, 4, 5, 6, 7 or 8, L having a structure selected from —CF(CF$_3$)—, —CF$_2$—, —CF$_2$CF$_2$— and —CHFCF$_2$, Rf—(O—CF$_2$CF$_2$)$_n$—O—CF$_2$-T, with n=1, 2, 3, 4 or 5 and Rf being a linear or branched per- or partly fluorinated alkyl rest (including C1 to C6 or C1 to C4), wherein the alkyl chain can be interrupted by O atoms, an oligomeric compound obtainable by the anionic or photochemical (in the presence of oxygen) polymerization or copolymerisation of monomers selected from vinylidenfluoride, hexafluoropropylenoxide, tetrafluoroethylene, 2,2,3,3-tetrafluorooxetane, trifluoroethylene or monofluoroethylene, wherein at least one chain-end of the oligomeric compound is represented by a function T, T being selected from the group consisting of —COOR, —CONR$^b$R$^c$—CH$_2$OH, —CF$_2$OR, —CHFOH, —CHFOR, —CH$_2$OR or —F with R and being a linear or branched alkyl rest (C1 to C9), aryl rest (C1 to C9) or alkylaryl rest (C1 to C9) each of which may optionally be substituted with one or more substituents selected from the group consisting of hydroxyl, amino group, halogen atom, an SiH group and a group capable of reacting with SiH, R$^b$ and R$_c$ independently representing H or having a meaning as given for R.

Specific examples of T include:

a) homo- or copolymerization of hexafluoropropylenoxide and/or 2,2,3,3-tetrafluorooxetane;
b) homo- or copolymerization of vinylidenfluoride, hexafluoropropylenoxide, tetrafluoroethylene, 2,2,3,3-tetrafluorooxetane, trifluoroethylene and/or monofluoroethylene in the presence of oxygen In particular, the esters, especially the methylesters, and the amidols (T=C(O)NH-alkyl-OH) and the respective alcohols or methylethers, prepared by chemical reduction, of the following structures can be used.

Further examples can be found in EP 2 231 102 B1. The content of this reference with respect to the description of F-containing components is herewith incorporated by reference.

The F-containing components described above typically function as wetting-enabler, that is, they do not show hydrophiliating properties if used alone (i.e. without an additional surfactant), but increase the hydrophilating properties of an additionally added surfactant.

Particularly useful are hexafluoropropylene oxide (HFPO) derivatives including carboxyl ester derivatives and amidol derivatives of HFPO.

HFPO can be obtained as described in U.S. Pat. No. 3,242,218 or US 2004/0124396. The general formula of a methyl ester derivative of HFPO is C$_3$F$_7$O[CF(CF$_3$)CF$_2$O]$_n$CF(CF$_3$)COOCH$_3$ with n being 2 to 14.

Astringent(s) which may be present include aluminium salts like aluminium sulfate, aluminium ammonium sulfated, aluminium chlorohydrated, aluminium acetate and mixtures thereof. Useful astringent(s) can also contain iron, manganese and/or zink containing substances.

The paste(s) may comprise a flavorant or mixtures of flavorants to improve the taste and/or smell of the composition. Flavorants, which can be used, include isoamylacetate (banana), benzaldehyde (bitter almond), cinnamic aldehyde (Cinnamon), ethylpropionate (fruity), methyl anthranilate (Grape), mints (e.g. peppermints), limonene (e.g. Orange), Allylhexanoate (pineapple), ethylmaltol (candy), ethylvanillin (Vanilla), methylsalicylate (Wintergreen).

Examples of colourants which can be used include chinoline yellow dye (sicovit), chromophthalblue A3R, red iron oxide 3395, Bayferrox 920 Z Yellow, Neazopon Blue 807 (copper phthalocyanine-based dye), Helio Fast Yellow ER, Brilliant Blue FCF, Fast Green FCF and/or Orange Yellow S. Pigments or dyes which are stable under acidic conditions are preferred.

The use of colourants is sometimes preferred, as it may facilitate the visibility of the composition in the mouth of the patient, in particular, if the composition is used for dental retraction purposes.

If present, the additive component(s) (i) may be present in the following amounts:
Lower amount: at least 0.01 or at least 0.1 or at least 1 wt.-%;
Upper amount: utmost 20 or utmost 15 or utmost 10 wt.-%;
Range: from 0.01 to 20 or from 0.1 to 15 or from 1 to 10 wt.-%
wt.-% with respect to the weight of Paste (A), Paste (B) or Paste (C).

Pastes (A), (B) and (C) can be produced by mixing the individual components of the paste(s), e.g. by using a speed-mixer or kneader.

Pastes (A), (B) and (C) are typically stored until use in suitable packaging devices. Suitable packaging devices include syringes, foil bags, tubes or cartridges.

Those packaging devices are either inserted into a manually or electrically driven dispensing device (e.g. if a foil bag or cartridge is used) or function as delivery or dispensing system on its own (e.g. if a syringe is used).

To enable an adequate mixing of the respective compositions, the packaging devices are typically equipped with a static or dynamic mixer.

Thus, the invention is also directed to a system for storing and delivering Paste A, Paste B and Paste C as described in the present text.

A suitable system comprises three compartments for storing the respective pastes, means for delivering the respective pastes to an outlet orifice and an interface for receiving a mixing tip.

Means for delivering the pastes include plungers and pistons which fit into the compartments of the system.

In order to be able to adjust the mixing ration between Pastes (A), (B) and (C), the means for delivering may be set up to work independent from another.

According to one embodiment, the means for delivering Pastes (A) and (B) are connected to each other to enable the delivery of Pastes (A) and (B) in a fixed and predefined volume ratio.

In this embodiment, the means for delivering Paste (C) can be used independent from the other means for delivery and allows for a separate dosing of Paste (C).

The kit of parts and the respective system for storing and delivering as described in the present text is to be used in a dental impression and retraction process.

The process for taking a dental impression of a dental situation including sub-gingival parts of the sulcus described in the present text comprises a couple of steps.

In a first step, the kit of parts described in the present text is provided.

In a next step Paste (A), Paste (B) and Paste (C) are mixed to obtain Composition (ABC).

In a further step Composition (ABC) is applied into the sulcus of a dental situation.

In a further step Paste (A) and Paste (B) are mixed to obtain Composition (AB).

Composition (AB) is put in contact with Composition (ABC). Typically, Composition (AB) is put on top of Composition (ABC) which has been applied into the sulcus.

Composition (AB) and Composition (ABC) remain in the mouth of the patient until the compositions are hardened.

The hardened compositions are removed from the mouth of the patient.

As a result an impression is obtained which comprises two sections, hardened Composition (ABC) and hardened Composition (AB). The impression is a negative image of the dental situation including the sub-gingival parts, i.e. those parts of the dental situation which are typically not easily accessible as they are located below the gum line.

To obtain Composition (ABC), Paste (A), Paste (B) and Paste (C) are typically mixed in the following ratios: (A+B):C from 1:1 to 20:1 by volume, wherein Paste (A) and Paste (B) are typically mixed in the following ratios: from 10:1 to 1:5.

To obtain Composition (AB), Paste (A) and Paste (B) are typically mixed in the following ratios: from 10:1 to 1:5 by volume.

Composition (ABC) is usually applied in a smaller amount than Composition (AB).

With respect to a process comprising the taking of a dental impression of one tooth, the volume ratio of Composition (ABC) to Composition (AB) is typically from 1:2 to 1:100. Preferably, the volume ratio of Composition (ABC) to Composition (AB) is typically from 1:3 to 1:50.

Composition (ABC) can typically be characterized by at least one, more or all of the following parameters:
  Consistency according to ISO 4823: <30 mm;
  Shore hardness A determined 10 min after mixing: >20;
  Residual gap resistance: >0.5 mm;
  having a water contact angle, measured 10 s after placing a drop of water onto the surface of the paste, of <90.

The process for determining the residual gap resistance behaviour can be described as follows:
  providing a mould having a rectangular shape with the dimensions x (depth)=7.5 mm, y (width)=18 mm and z (height)=12 mm, the mould being formed by three immovable and one movable sidewall, all located on a plane surface, the movable sidewall being equipped with a spring having a defined spring pressure of 20 N,
  x being the distance between the movable sidewall and the opposing immobile sidewall,
  compressing and fixing the spring,
  mixing the components of composition (A) and filling composition (A) into the mould,
  removing the fixation of the spring 60s after mixing of the components of composition (A),
  measuring the value x 70s after mixing of the components of composition (A).

Composition (AB) can be characterized by at least one, more or all of the following parameters:
  Consistency according to ISO 4823: >31 mm;
  Shore hardness A determined 10 min after mixing: >20;
  Residual gap behaviour: less than or equal to 0.2 mm;
  having a water contact angle, measured 10 s after placing a drop of water onto the surface of the paste, of <90.

If desired, the above parameters can be determined as described in the Example section.

In some embodiments, it can be desirable to use a further curable composition for removing Composition (ABC) and Composition (AB) from the dental situation.

Thus, the process described in the present text may further comprise the steps of
  applying a further Composition (D) being different from Composition (AB) and Composition (ABC) in contact with Composition (AB), and
  removing Composition (ABC), Composition (AB) and Composition (D) from the dental situation.

Composition (D) is typically located in a dental tray when brought in contact with the other compositions.

It can be beneficial, if Composition (D) is of a similar chemical nature as Composition (ABC) and Composition (AB). This may contribute to a better adherence of the different compositions.

Composition (D) is typically used in a larger volume compared to Composition (ABC) and Composition (AB).

Composition (D) can be characterized by at least one, more or all of the following features:
being curable by an addition crosslinking reaction;
obtainable by mixing a base paste and a catalyst paste;
comprising components (a), (b), (e), optionally (d), (h) and (i) as described in the present text.

Composition (D) can be characterized by at least one, more or all of the following features:
having a consistency determined according to ISO 4823 of below or equal to 41 mm;
having a colour being different from the colour of Composition (AB) and Composition (ABC);

A preferred embodiment of the invention is directed to a kit of parts comprising Paste (A), Paste (B) and Paste (C), the pastes being characterized as follows: Paste (A) comprising
  at least one polyorganosiloxane with at least two olefinically unsaturated groups,
  at least one organohydrogenpolysiloxane,
  at least one alkylsiloxane having at least one carbinol, silanol, carboxyl or amino group or at least one alkylsiloxane having at least one silanol group,
  filler(s),
  Paste (A) having a consistency of 25 to 50 mm according to ISO 4823, Paste (B) comprising
  at least one polyorganosiloxane optionally with olefinically unsaturated groups,
  a Pt containing addition cure catalyst,
  optionally at least one alkylsiloxane having at least one carbinol, silanol, carboxyl or amino group or at least one alkylsiloxane haven at least one silanol group,
  filler(s), and
  Paste (B) having a consistency of 25 to 50 mm according to ISO 4823, Paste (C) comprising
  softener,
  a Ti, Zr, Zn or Sn containing condensation cure catalyst,
  filler(s), and
  optionally at least one polyorganosiloxane optionally comprising olefinically unsaturated groups,
  Paste (C) having a consistency of 25 to 50 mm according to ISO 4823, the kit of parts being provided or is intended for producing a composition for conducting a dental retraction and dental impressioning process as described in the present text.

All components used in the dental composition of the invention should be sufficiently biocompatible, that is, the composition should not produce a toxic, injurious, or immunological response in living tissue.

The process described in the present text does typically not comprise either of the following steps:
  application or use of a dental retraction cord or of a dental compression cap;
  use of compositions being able to expand in volume more than 5% of their original volume after mixture.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 1013 mbar).
Methods
Shore Hardness A
If desired, the Shore hardness can be determined according to DIN 53505.
Consistency
The consistency of pastes to be mixed is determined according to ISO 4823. If the consistency is to be determined for a single paste, the same procedure is applied, however, leaving out the steps of mixing the pastes and waiting at least 15 min for the material to fully cure before measuring the diameter of the composition under a pre-defined load.
Residual Gap Behavior
The capability of a curable paste to open a sulcus and to keep a sulcus open during setting time of the paste can be determined by a device using a stamp which creates pressure created by a spring onto the curable paste in a small slit (residual gap device).

More precisely, the method can be described as follows:
The gap resistance can be determined as follows:
A mold having a rectangular shape with the dimensions: x (depth)=7.5 mm, y (width)=18.0 mm and z (height)=12.0 mm is provided.

The mold (1) is formed by three immovable sidewalls (1a), (1b), (1c) and one movable sidewall (1d), all located on a plane surface (2). The movable sidewall (1d) is equipped with a spring (3) having a defined spring pressure of 20N. The spring is compressed and fixed by a removable fixation means (4). The moveable sidewall (1d) is adjusted to a pre-defined depth of 7.5 mm (x-direction). A device for determining the consistency is shown in FIG. 1.

The mold is filled with the curable composition.
After a pre-defined time T1, the fixation means (4) of the spring (3) is removed having the result that the spring (3) exerts a predefined pressure on the curable composition through the movable sidewall (1d). A portion of the curable composition is pressed out of the mold (1). The depth of the mold is decreasing which can be determined by measuring the distance for x (mm) using e.g. a length gauge (5).

After a pre-defined time T2, the value for x (mm) is determined.

The higher the value x at time T2 is, the higher the consistency/residual gap behaviour of the composition is.

For all results reported below, T1=60 s from start of mixing; T2=70 s from start of mixing.
Mean Particle Size
If desired, the mean or average particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).
Viscosity
If desired, the viscosity can be measured at 23° C. using a ThermoHaake Rotovisco 1 device with a plate/plate system (diameter 20 mm) and a slit of 0.2 mm. The viscosity values (Pas) and share stress values (Pa) can be recorded for each share rate (starting from 10 l/s to 100 l/s in 10 l/s steps. For each share rate, a delay of 5 seconds was used before collecting data. The above mentioned method of measurement corresponds essentially to DIN 53018-1.
Water Contact Angle
If desired, the water contact angle of the uncured paste can be measured as follows: Test specimen preparation: For the preparation of test piece the mixed paste is subjected to an object slide and flattened and triturated by a second object slide in order to obtain a thin film. The test piece preparation is performed in that simplified way as the thickness of the film does not have a significant effect on the measured water contact angle (see G. Kugel, T. Klettke, J. A. Goldberg, J. Benchimol, R. D. Perry, S. Sharma, J. Prosthod. 2007, 16, 84-92). Measurement: The object slide is placed on the table of a Drop Shape Analyse System DSA 10 (Krüss GmbH, Hamburg), a well known device for measuring contact angles. 5 µl of water are placed onto the surface of the specimen and an automatic contact angle measurement is started using standard software of the goniometer. Measuring time is at least about 10 s up to about 200 s. The water contact angle is measured at different time periods after mixing of base paste and catalyst paste, especially after 25 s. The data (video sequences) is evaluated by the "circle fitting" method, another standard method for data evaluation (see G. Kugel, T. Klettke, J. A. Goldberg, J. Benchimol, R. D. Perry, S. Sharma, J. Prosthod. 2007, 16, 84-92); Θ 2 s is the angle obtained 2 s after placing the water drop on the surface.
Materials

| Name | Description |
| --- | --- |
| Vinyl-terminated Polydimethylsiloxane, 10,000 mPa*s | Curable organic matrix (I) |
| Vinyl-terminated Polydimethylsiloxane, 200 mPa*s | Curable organic matrix (I) |
| Vinyl-terminated Polydimethylsiloxane, 1,000 mPa*s | Curable organic matrix (I) |
| Vinyl-terminated Polydimethylsiloxane, 2,000 mPa*s | Curable organic matrix (I) |

| Name | Description |
|---|---|
| Polydimethylsiloxane silanol terminated 50,000 mPa*s | Curable organic matrix (II) |
| Polydimethylsiloxane dicarbinol terminated, 3,200 mPa*s | Curable organic matrix (II) |
| Organohydrogenpolysiloxane (SiH: 1.9 mmol/g) | Curable organic matrix (I) |
| Organohydrogenpolysiloxane (SiH: 3.8 mmol/g) | Curable organic matrix (I) |
| Cristobalite filler | Filler |
| Hydrophobic fumed silica | Filler |
| Silane treated Cristobalite filler | Filler |
| Stabilizer | Additive |
| Antioxidant | Additive |
| Ethoxylated Surfactant | Additive |
| Tetraallylsilane | Additive |
| Platinum tetramethyldivinyldisiloxane complex 1.3 wt.-% Pt in silicone oil containing in addition 2.875 wt.-% of VMO | Addition cure catalyst |
| Hydrogen scavenger | Additive |
| Mineral oil | Softener |
| Vaseline | Softener |
| Blue pigment | Additive |
| zeolite | Filler |
| Titanium isopropoxide | Condensation cure catalyst |

General Description of Preparation

All Examples are prepared by homogenizing the respective components to a uniform paste using a planetary mixer with vacuum capabilities (Speedmixer DAC 600.1 VAC-P).

Base Composition A1

| Component | weight % |
|---|---|
| Vinyl-terminated Polydimethylsiloxane, 10,000 mPa*s | 30.750 |
| Vinyl-terminated Polydimethylsiloxane, 200 mPa*s | 8.500 |
| Polydimethylsiloxane silanol-terminated, 50,000 mPa*s | 8.000 |
| Organohydrogenpolysiloxane (SiH: 1.9 mmol/g) | 5.500 |
| Organohydrogenpolysiloxane (SiH: 3.8 mmol/g) | 6.000 |
| Hydrophobic fumed silica | 2.750 |
| Cristobalite filler | 35.500 |
| Phosphite Stabilizer | 0.012 |
| Antioxidant | 0.012 |
| Ethoxylated Surfactant | 2.976 |

Catalyst Composition B1

| Component | weight % |
|---|---|
| Vinyl-terminated Polydimethylsiloxane, 1000 mPa*s | 0.186 |
| Vinyl-terminated Polydimethylsiloxane, 10,000 mPa*s | 19.200 |
| Vinyl-terminated Polydimethylsiloxane, 2,000 mPa*s | 21.800 |
| Polydimethylsiloxane silanol terminated 50,000 mPa*s | 8.000 |
| Pigment dispersion in polydimethylsiloxane (30,000 to 100,000 mPas) | 0.600 |
| Hydrophobic fumed silica | 3.510 |
| Cristobalite filler | 44.600 |
| Tetraallylsilane | 0.500 |
| Platin tetramethyldivinyldisiloxane complex 1.3 wt.-% Pt in silicone oil containing in addition 2.875 wt.-% of VMO | 1.60 |
| Hydrogen scavenger | 0.004 |

Viscosity Modifier Composition C

| Component | weight % |
|---|---|
| Mineral oil | 23.000 |
| Vaseline | 12.000 |
| Blue Pigment | 0.050 |

| Component | weight % |
|---|---|
| Hydrophobic fumed silica | 6.000 |
| Silane treated Cristobalite filler | 53.950 |
| Zeolite | 2.000 |
| Titanium isopropoxide | 3.000 |

Base Composition A2

| Component | weight % |
|---|---|
| Vinyl-terminated Polydimethylsiloxane, 10,000 mPa*s | 32.750 |
| Vinyl-terminated Polydimethylsiloxane, 200 mPa*s | 8.500 |
| Polydimethylsiloxan dicarbinol terminiert, 3,200 mPa*s | 6.000 |
| Organohydrogenpolysiloxane (SiH: 1.9 mmol/g) | 5.500 |
| Organohydrogenpolysiloxane (SiH: 3.8 mmol/g) | 6.000 |
| Hydrophobic fumed silica | 2.750 |
| Cristobalite filler | 35.500 |
| Phosphite Stabilizer | 0.012 |
| Antioxidant | 0.012 |
| Ethoxylated Surfactant | 2.976 |

Base Composition A3

| Component | weight % |
|---|---|
| Vinyl-terminated Polydimethylsiloxane, 10,000 mPa*s | 28.500 |
| Vinyl-terminated Polydimethylsiloxane, 200 mPa*s | 10.000 |
| Polydimethylsiloxan dicarbinol terminiert, 3,200 mPa*s | 8.000 |
| Organohydrogenpolysiloxane (SiH: 1.9 mmol/g) | 5.500 |
| Organohydrogenpolysiloxane (SiH: 3.8 mmol/g) | 6.000 |
| Hydrophobic fumed silica | 3.500 |
| Cristobalite filler | 35.500 |
| Phosphite Stabilizer | 0.012 |
| Antioxidant | 0.012 |
| Ethoxylated Surfactant | 2.976 |

Catalyst Composition B2

| Component | weight % |
|---|---|
| Vinyl-terminated Polydimethylsiloxane, 10,000 mPa*s | 23.2 |
| Vinyl-terminated Polydimethylsiloxane, 1,000 mPa*s | 0.186 |
| Hydrophobic fumed silica | 0.01 |
| Hydrogen scavenger | 0.004 |
| Vinyl-terminated Polydimethylsiloxane, 2,000 mPa*s | 25.8 |
| Pigment dispersion in polydimethylsiloxane (30,000 to 100,000 mPas) | 0.6 |
| Hydrophobic fumed silica | 3.51 |
| Cristobalite filler | 44.6 |
| Tetraallylsilane | 0.5 |
| Platinum tetramethyldivinyldisiloxane complex 1.3 wt.-% Pt in silicone oil containing in addition 2,875 wt.-% of VMO | 1.60 |

Catalyst Composition B3

| Component | weight % |
|---|---|
| Vinyl-terminated Polydimethylsiloxane, 1,000 mPa*s | 0.186 |
| Hydrogen scavenger | 0.004 |
| Vinyl-terminated Polydimethylsiloxane, 10,000 mPa*s | 21.200 |
| Vinyl-terminated Polydimethylsiloxane, 2,000 mPa*s | 21.800 |
| Pigment dispersion in polydimethylsiloxane (30,000 to 100,000 mPas) | 0.600 |
| Hydrophobic fumed silica | 3.510 |
| Cristobalite filler | 44.600 |
| Tetraallylsilane | 0.500 |
| Platinum tetramethyldivinyldisiloxane complex 1.3 wt.-% Pt in silicone oil containing in addition 2.875 wt.-% of VMO | 1.600 |
| Polydimethylsiloxane dicarbinol terminiert | 6.000 |

Catalyst Composition B4

| Component | weight % |
|---|---|
| Vinyl-terminated Polydimethylsiloxane, 1,000 mPa*s | 0.186 |
| Hydrogen scavenger | 0.004 |
| Vinyl-terminated Polydimethylsiloxane, 10,000 mPa*s | 16.200 |
| Vinyl-terminated Polydimethylsiloxane, 2,000 mPa*s | 24.800 |
| Pigment dispersion in polydimethylsiloxane (30,000 to 100,000 mPas) | 0.600 |
| Hydrophobic fumed silica | 3.510 |
| Cristobalite filler | 44.600 |
| Tetraallylsilane | 0.500 |
| Platinum tetramethyldivinyldisiloxane complex 1.3 wt.-% Pt in silicone oil containing in addition 2.875 wt.-% of VMO | 1.600 |
| Polydimethylsiloxane dicarbinol terminiert | 8.000 |

Compositions A and B were mixed in a 1:1 ratio by weight.

Composition A, B and C were mixed in a 2.5:2.5:1 ratio by weight.

Results:

| | Consistency (ISO4823) | | | | | |
|---|---|---|---|---|---|---|
| | Example 1 [mm] | | Example 2 [mm] | | Example 3 [mm] | |
| | Result [mm] | Composition | Result [mm] | Composition | Result [mm] | Composition |
| without Modifier | 39 | A1 + B1 | 41 | A2 + B2 | 39 | A2 + B3 |
| with Modifier | 22 | A1 + B1 + C | 27 | A2 + B2 + C | 21 | A2 + B3 + C |

| | Consistency (ISO4823)/Residual Gap Example 4 [mm] | | |
|---|---|---|---|
| | Consistency Result [mm] | Residual Gap Result [mm] | Composition |
| without Modifier | 44 | 0.02 | A3 + B4 |
| with Modifier | 18 | 3.64 | A3 + B4 + C |

Finding:

It is shown that the consistency of a composition prepared by mixing the respective Catalyst and Base Compositions A and B can be increased by adding a Modifier Composition C. At the same time the capability of the resulting composition to keep the sulcus of a tooth open is increased as demonstrated by the so-called Residual Gap Resistance behaviour.

The invention claimed is:

1. A kit of parts comprising Paste (A), Paste (B) and Paste (C) for conducting a dental impression and retraction process, comprising:
   Paste (A) comprising:
      at least one polyorganosiloxane with at least two olefinically unsaturated groups;
      at least one organohydrogenpolysiloxane; and
      at least one alkylsiloxane having at least one carbinol, silanol, alkoxy, carboxyl or amino group;
   Paste (B) comprising:
      at least one polyorganosiloxane optionally with olefinically unsaturated groups and
      at least one addition cure catalyst;
   and
   Paste (C) comprising:
      a softener; and
      a condensation cure catalyst;
      wherein the condensation cure catalyst being characterized by at least one of the following features:
         being present in an amount from 0.1 to 15.0 wt.-% with respect to the weight of Paste (C);
         comprising a Ti, Zr, Zn or Sn containing component.

2. The kit of parts of claim 1, the addition cure catalyst being characterized by at least one of the following features:
   comprising a Pt containing component;
   being present in an amount from 0.00005 to 0.05 calculated as elemental platinum with respect to the weight of Paste (B).

3. The kit of parts claim 1, Paste (A) being characterized by at least one of the following features:
   having a consistency according to ISO 4823 in the range from 25 to 50 mm;
   having a water contact angle, measured 10 s after placing a drop of water onto the surface of the paste of <90°.

4. The kit of parts of claim 1, Paste (B) having a consistency of 25 to 50 mm, if determined according to ISO 4823.

5. The kit of parts of claim 1, Paste (C) having a consistency of 25 to 50 mm, if determined according to ISO 4823.

6. The kit of parts to the of claim 5, the additive(s) being selected from hydrophilating agent(s), retarder(s), inhibitor(s), colourant(s), stabilizer(s), flavouring(s), hydrogen scavenger(s), rheology modifier(s), astringent(s) and mixtures thereof.

7. A process for taking a dental impression of a dentition including sub-gingival parts of the sulcus, the process comprising:
   providing the kit of parts as described in claim 1;
   mixing Paste (A), Paste (B) and Paste (C) to obtain Composition (ABC);
   applying Composition (ABC) into the sulcus of the dentition;
   mixing Paste (A) and Paste (B) to obtain Composition (AB);
   applying Composition (AB) in contact with Composition (ABC;
   optionally applying a further Composition (D) being different from Composition (AB) and Composition (ABC) in contact with Composition (AB); and
   removing Composition (ABC) and Composition (AB) and Composition (D), if present, from the dentition.

8. The process of claim 7, wherein in step b) the mixing ratio of Paste (A), Paste (B) and Paste (C) is (A+B):C from 1:1 to 20:1 by volume, wherein Paste (A) and Paste (B) are mixed in a ratio from 10:1 to 1:5.

9. The process of claim 7, wherein in step d) the mixing ratio of Paste (A), Paste (B) is from 10:1 to 1:5 by volume.

10. The process of claim 7, wherein the Composition (ABC) is used in a smaller volume compared to Composition (AB).

11. The process of claim 7, Composition (ABC) being characterized by at least one or all of the following features:
Consistency according to ISO 4823 of <30 mm;
Shore hardness A determined 10 min after mixing: >20;
Residual gap resistance: larger than 0.50 mm;
Water contact angle, measured 10 s after placing a drop of water onto the surface of the paste, of <90°;
Colour of Composition (ABC) being different from colour of Composition (AB).

12. The process of claim 7, Composition (AB) being characterized by at least one or all of the following features:
Consistency according to ISO 4823 of >31 mm;
Shore hardness A determined 10 min after mixing: >20;
Residual gap behaviour: less than or equal to 0.2 mm;
Water contact angle, measured 10 s after placing a drop of water onto the surface of the paste, of <90.

13. A system for storing and delivering Paste (A), Paste (B) and Paste (C) as described in claim 1, the system comprising three compartments for storing the respective pastes, means for delivering the respective pastes to an outlet orifice and an interface for receiving a mixing tip.

14. A process of conducting a dental retraction and dental impression process, the process comprising:
mixing Paste (A), Paste (B) and Paste (C) to obtain Composition (ABC);
applying composition (ABC) into the sulcus of a dentition;
mixing Paste (A) and Paste (B) to obtain Composition (AB);
applying composition (AB) in contact with Composition (ABC);
and removing Composition (ABC) an Composition (AB) from the dentition,
wherein Paste (A) comprises:
at least one polyorganosiloxane with at least two olefinically unsaturated groups, and
　at least one organohydrogenpolysiloxane,
　at least one alkylsiloxane having at least one carbinol, silanol, alkoxy, carboxyl or amino group;
wherein Paste (B) comprises:
at least one polyorganosiloxane optionally with olefinically unsaturated groups,
　at least one addition cure catalyst
wherein Paste (C) comprises:
　a softener;
　a condensation cure catalyst
　wherein the condensation cure catalyst is characterized by at least one of the following features:
　　being present in an amount from 0.1 to 15.0 wt.-% with respect to the weight of Paste (C);
　　comprising a Ti, Zr, Zn or Sn containing component.

15. The kit of parts of claim 1, wherein Paste (A) further comprises filler(s).

16. The kit of parts of claim 1, wherein Paste (A) further comprises additive(s).

17. The kit of parts of claim 1, wherein Paste (B) further comprises at least one alkylsiloxane having at least one carbinol, silanol, alkoxy; carboxyl or amino group.

18. The kit of parts of claim 1, wherein Paste (B) further comprises filler(s).

19. The kit of parts of claim 1, wherein Paste (B) further comprises additive(s).

20. The kit of parts of claim 1, wherein Paste (C) further comprises filler(s).

21. The kit of parts of claim 1, wherein Paste (C) further comprises additive(s).

22. The kit of parts of claim 1, wherein Paste (C) further comprises at least one polyorganosiloxane optionally with olefinically unsaturated groups.

* * * * *